(12) United States Patent
Crawford et al.

(10) Patent No.: US 11,869,670 B2
(45) Date of Patent: *Jan. 9, 2024

(54) SYSTEMS AND METHODS FOR AUTOMATED SEGMENTATION OF PATIENT SPECIFIC ANATOMIES FOR PATHOLOGY SPECIFIC MEASUREMENTS

(71) Applicant: Axial Medical Printing Limited, Belfast (GB)

(72) Inventors: Daniel Crawford, Belfast (GB); Rory Hanratty, Belfast (GB); Luke Donnelly, Muff (GB); Luis Trindade, Craigavon (GB); Thomas Schwarz, Sussex (GB); Adam Harpur, Bangor (GB)

(73) Assignee: Axial Medical Printing Limited, Belfast (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/131,859

(22) Filed: Apr. 6, 2023

(65) Prior Publication Data

US 2023/0245784 A1    Aug. 3, 2023

Related U.S. Application Data

(63) Continuation of application No. 17/662,802, filed on May 10, 2022, now Pat. No. 11,626,212, which is a
(Continued)

(30) Foreign Application Priority Data

Feb. 11, 2021 (GB) ..................................... 2101908

(51) Int. Cl.
*G16H 50/50* (2018.01)
*G06T 7/00* (2017.01)
(Continued)

(52) U.S. Cl.
CPC ........... *G16H 50/50* (2018.01); *G06T 7/0016* (2013.01); *G06T 7/62* (2017.01); *G06T 15/04* (2013.01);
(Continued)

(58) Field of Classification Search
CPC ......... G06T 7/0016; G06T 7/62; G06T 15/04; G06T 15/06; G06T 17/20; G06T 2210/21;
(Continued)

(56) References Cited

U.S. PATENT DOCUMENTS 5,859,891 A   1/1999  Hibbard
9,437,119 B1  9/2016  Bernal
(Continued)

FOREIGN PATENT DOCUMENTS

EP         3020537 A1      5/2016
WO    WO-2016161198 A1    10/2016
(Continued)

OTHER PUBLICATIONS

Filing Date/Issue Date.
(Continued)

*Primary Examiner* — Sing-Wai Wu
(74) *Attorney, Agent, or Firm* — Eversheds Sutherland (US) LLP; Christopher C. Bolten; Albert K. Heng

(57) ABSTRACT

Systems and methods are provided for multi-schema analysis of patient specific anatomical features from medical images. The system may receive medical images of a patient and metadata associated with the medical images indicative of a selected pathology, and automatically classify the medical images using a segmentation algorithm. The system may use an anatomical feature identification algorithm to identify one or more patient specific anatomical features within the medical images by exploring an anatomical knowledge dataset. A 3D surface mesh model may be
(Continued)

generated representing the one or more classified patient specific anatomical features, such that information may be extracted from the 3D surface mesh model based on the selected pathology. Physiological information associated with the selected pathology for the 3D surface mesh model may be generated based on the extracted information.

30 Claims, 32 Drawing Sheets

Related U.S. Application Data continuation of application No. PCT/IB2022/051216, filed on Feb. 10, 2022.

(51) Int. Cl.

| | | |
|---|---|---|
| G06T 7/62 | (2017.01) | |
| G06T 15/04 | (2011.01) | |
| G06T 17/20 | (2006.01) | |
| G06V 10/26 | (2022.01) | |
| G06V 10/764 | (2022.01) | |
| G06V 20/70 | (2022.01) | |
| G16H 30/40 | (2018.01) | |
| G06T 15/06 | (2011.01) | |

(52) U.S. Cl.
CPC .............. *G06T 15/06* (2013.01); *G06T 17/20* (2013.01); *G06V 10/26* (2022.01); *G06V 10/764* (2022.01); *G06V 20/70* (2022.01); *G16H 30/40* (2018.01); *G06T 2210/21* (2013.01); *G06T 2210/41* (2013.01); *G06V 2201/03* (2022.01)

(58) Field of Classification Search
CPC .... G06T 2210/41; G16H 50/50; G16H 30/40; G06V 10/26; G06V 10/764; G06V 20/70; G06V 2201/03
See application file for complete search history.

(56) References Cited

U.S. PATENT DOCUMENTS

| | | | |
|---|---|---|---|
| 9,646,411 | B2 | 5/2017 | Lee |
| 10,032,281 | B1 | 7/2018 | Ghesu et al. |
| 10,409,235 | B2 | 9/2019 | Zhou et al. |
| 10,946,586 | B2 | 3/2021 | Casey et al. |
| 10,981,680 | B2 | 4/2021 | Colson et al. |
| 11,010,800 | B2 | 5/2021 | Norman |
| 11,059,228 | B2 | 7/2021 | Elber et al. |
| 11,138,790 | B2 | 10/2021 | Haslam et al. |
| 11,288,865 | B2 | 3/2022 | Haslam et al. |
| 11,436,801 | B2 | 9/2022 | Haslam et al. |
| 11,497,557 | B2 | 11/2022 | Haslam et al. |
| 11,551,420 | B2 | 1/2023 | Haslam et al. |
| 2009/0316975 | A1 | 12/2009 | Kunz et al. |
| 2010/0156904 | A1 | 6/2010 | Hartung |
| 2011/0038516 | A1 | 2/2011 | Koehler et al. |
| 2011/0218428 | A1 | 9/2011 | Westmoreland et al. |
| 2012/0059252 | A1 | 3/2012 | Li et al. |
| 2012/0224755 | A1 | 9/2012 | Wu |
| 2013/0002646 | A1 | 1/2013 | Lin et al. |
| 2014/0328529 | A1 | 11/2014 | Koceski et al. |
| 2014/0361453 | A1 | 12/2014 | Triantafyllou |
| 2015/0089337 | A1 | 3/2015 | Grady et al. |
| 2015/0169985 | A1 | 6/2015 | Burger et al. |
| 2015/0342537 | A1 | 12/2015 | Taylor et al. |
| 2016/0086078 | A1 | 3/2016 | Ji et al. |
| 2016/0300350 | A1 | 10/2016 | Choi et al. |
| 2017/0007129 | A1 | 1/2017 | Kaib et al. |
| 2017/0228505 | A1 | 8/2017 | Allen et al. |
| 2017/0329930 | A1 | 11/2017 | Fonte et al. |
| 2018/0165867 | A1 | 6/2018 | Kuhn et al. |
| 2018/0276815 | A1 | 9/2018 | Xu et al. |
| 2018/0365835 | A1 | 12/2018 | Yan et al. |
| 2019/0053855 | A1 | 2/2019 | Siemionow et al. |
| 2019/0105009 | A1 | 4/2019 | Siemionow et al. |
| 2019/0108635 | A1 | 4/2019 | Hibbard et al. |
| 2019/0205606 | A1 | 7/2019 | Zhou et al. |
| 2019/0251694 | A1 | 8/2019 | Han et al. |
| 2019/0392942 | A1 | 12/2019 | Sorenson et al. |
| 2020/0074637 | A1 | 3/2020 | Wong |
| 2020/0367970 | A1 | 11/2020 | Qiu et al. |
| 2020/0402647 | A1 | 12/2020 | Domracheva et al. |
| 2021/0068714 | A1 | 3/2021 | Crowley et al. |
| 2021/0074425 | A1* | 3/2021 | Carter .................. G06V 10/25 |
| 2021/0097690 | A1 | 4/2021 | Mostapha et al. |
| 2021/0110605 | A1 | 4/2021 | Haslam et al. |
| 2021/0335041 | A1 | 10/2021 | Haslam et al. |

FOREIGN PATENT DOCUMENTS

| | | | |
|---|---|---|---|
| WO | WO-2018069736 | A1 | 4/2018 |
| WO | WO-2018222779 | A1 | 12/2018 |
| WO | WO-2020144483 | A1 | 7/2020 |

OTHER PUBLICATIONS 11,497,557 Apr. 12, 2019 / Nov. 15, 2022.
11,138,790 Dec. 08, 2020 / Oct. 05, 2021.
11,436,801 Jul. 09, 2021 / Sep. 06, 2022.
11,288,865 Sep. 30, 2021 / Mar. 26, 2022.
11,551,420 Mar. 23, 2022 / Jan. 10, 2023.
11,626,212 May 10, 2022 / Apr. 11, 2023.
/Sing -I Wu/ Jun. 08, 2023.
Baghaie, et al., An Optimization Method for Slice Interpolation of Medical Images, arXiv preprint arXiv:1402.0936 (Feb. 2014).
Boulton, et al., Lessons from the National Hip Fracture Database, Orthopaedics and Trauma, 30(2):123-127 (Apr. 2016).
Carvalho, et al., Estimating 3D lumen centerlines of carotid arteries in free-hand acquisition ultrasound, International Journal of Computer Assisted Radiology and Surgery, 7(2):207-215 (Mar. 2012).
Cui, et al., Brain MRI Segmentation with Patch-Based CNN Approach, Proceedings of the 35th Chinese Control Conference, Jul. 27-29, 2016, pp. 7026-7031.
Dou, et al., 3D Deeply Supervised Network for Automated Segmentation of Volumetric Medical Images, Medical Image Analysis, 41:40-54 (Oct. 2017).
Geremia, et al., Spatial Decision Forests for MS Lesion Segmentation in Multi-Channel Magnetic Resonance Images, NeuroImage, 57(2):378-390 (Jul. 2011).
International Search Report & Written Opinion dated Feb. 16, 2018 in Int'l PCT Patent Appl. Serial No. PCT/GB2017/053125 (0110).
International Search Report & Written Opinion dated May 12, 2022 in Int'l PCT Patent Appl. Serial No. PCT/IB2022/051216 (0310).
International Search Report & Written Opinion dated Jun. 25, 2020 in Int'l PCT Patent Appl. Serial No. PCT/GB2020/050063 (0210).
Laosai et al., Acute Leukemia Classification by Using SVM and K-Means Clustering, 2014 Proceedings of the International Electrical Engineering Congress (IEECON), pp. 1-4 (Mar. 19, 2014).
Lee, et al., Human Airway Measurement from CT Images. In Medical Imaging 2008: Computer-Aided Diagnosis, Proc. SPIE 6915:386-383 (Mar. 2008).
Litjens, et al., A Survey on Deep Learning in Medical Image Analysis, Medical Image Analysis, 42:60-88 (Dec. 2017).
Milletari, et al., V-Net: Fully Convolutional Neural networks for Volumetric Medical Image Segmentation, arXiv preprint arXiv: 1606.04797 (Jun. 2016).
Rogowska, et al., Overview and Fundamentals of Medical Image Segmentation, Handbook of Medical Imaging, Processing and Analysis, pp. 69-85 (Oct. 2000).
Schmauss D., et al., "Three-Dimensional Printing in Cardiac Surgery and Interventional Cardiology: A Single-Centre Experience," European Journal of Cardio-Thoracic Surgery, Aug. 26, 2014, vol. 47(6), pp. 1044-1052.

(56) References Cited

OTHER PUBLICATIONS

Yu, et al., 3D FractalNet: Dense Volumetric Segmentation for Cardiovascular MRI Volumes, In Reconstruction, Segmentation, and Analysis of Medical Images, pp. 103-110 (Oct. 2016).

Zhou, et al., Deep convolutional neural network for segmentation of knee joint anatomy, Mag. Reson. Med., 80(6):2759-2770 (Dec. 2018).

Brown, et al., Using Machine Learning for Sequence-Level Automated MRI Protocol Selection in Neuroradiology, Journal of the American Medical Informatics Association, 25(5):568-71 (May 2018).

Yu, et al., 3D FractaNet: dense volumetric segmentation for cardiovascular MRI volumes. In Reconstruction, Segmentation, and Analysis of Medical Images. First International Workshops, RAMBO 2016 and HVSMR 2016. Held in Conjunction with MICCAI 2016, Athens, Greece, Oct. 17, 2016, Revised Select.

\* cited by examiner

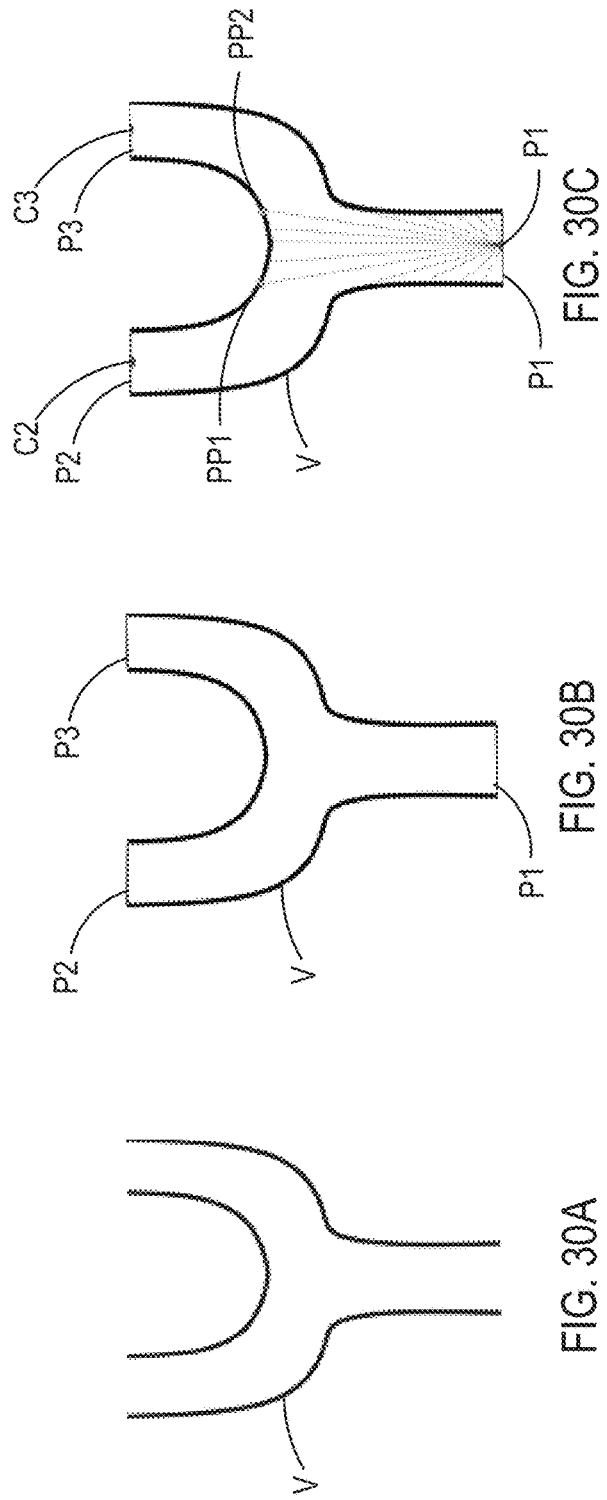
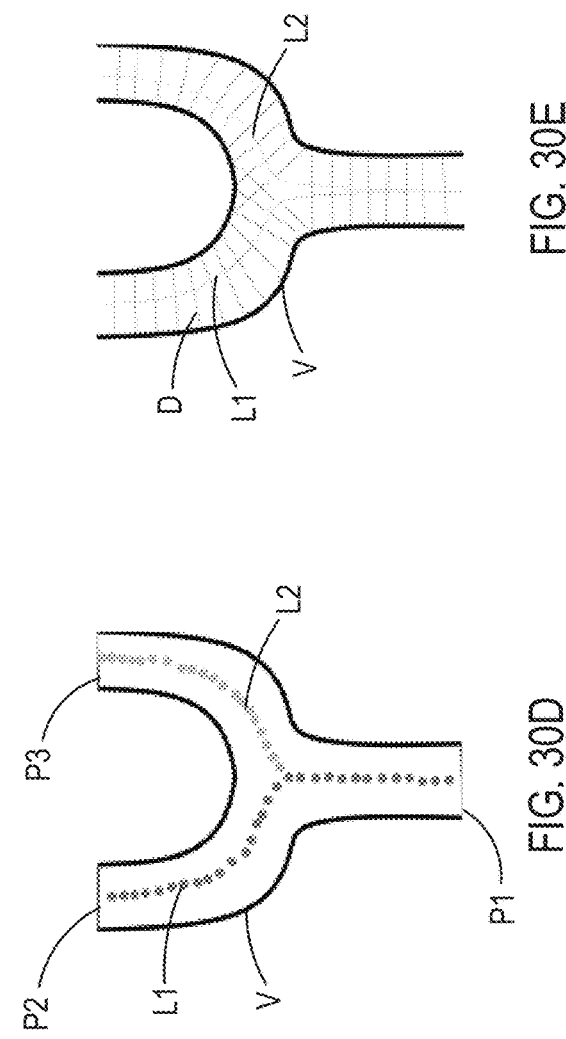

Example of using the hollow bone labeling schema

SYSTEMS AND METHODS FOR AUTOMATED SEGMENTATION OF PATIENT SPECIFIC ANATOMIES FOR PATHOLOGY SPECIFIC MEASUREMENTS

CROSS-REFERENCE TO RELATED APPLICATIONS

This application is a continuation of U.S. patent application Ser. No. 17/662,802, filed May 10, 2022, now U.S. Pat. No. 11,626,212, which is a continuation of International PCT Patent Application Serial No. PCT/IB2022/051216, filed Feb. 10, 2022, which claims the benefit of priority of GB Patent Application Serial No. 2101908.8, filed Feb. 11, 2021, the entire contents of each of which are incorporated herein by reference.

FIELD OF USE

The present disclosure is directed to systems and methods for multi-schema analysis of patient specific anatomical features from medical images for pathology specific measurements for specific use cases in diagnosis, planning and treatment.

BACKGROUND

Creating accurate 3D models of specific parts of a patient's anatomy is helping to transform surgery procedures by providing insights to clinicians for preoperative planning. Benefits include, for example, better clinical outcomes for patients, reduced time and costs for surgery and the ability for patients to better understand a planned surgery.

However, there is still a need to provide 3D models providing greater insight on the patient anatomy or pathology.

In view of the foregoing drawbacks of previously known systems and methods, there exists a need for enhanced systems and methods for analyzing medical images of a patient to create 3D models to assist in diagnosis, planning, and/or treatment.

SUMMARY

The present disclosure overcomes the drawbacks of previously-known systems and methods by providing systems and methods for multi-schema analysis of patient specific anatomical features from medical images for pathology specific measurements for specific use cases in diagnosis, planning, and/or treatment.

The generation of a scale virtual replica of the patient's anatomy, e.g., a 3D anatomical model, is an extremely useful tool that can be used to drive personalized patient specific decisions in clinical practice, e.g., for pre-operative planning. The present disclosure demonstrates how to generate patient specific 3D models of a patient's complete anatomy, for example, by building machine learning models to automatically detect and segment anatomy from medical scans. These models may be trained using curated semantically labeled datasets. To produce a 3D segmentation, a neural network or machine learning algorithm is trained to identify the anatomical features within a set of medical images. These images are semantically labeled with the location of the anatomical features and their constituent parts and landmarks. Accordingly, the segmentation algorithm can take new datasets and their complementary landmarks and use those to identify new anatomical features or landmarks.

The segmentation process is the first step in producing patient specific insights into anatomical features, which power decision making in the clinical setting. The technology made available by Axial Medical Printing Limited, Belfast, United Kingdom, turns the 2D medical scans into scale 3D models of the patient's anatomy, which allows 3D decision making and understanding. The output of the segmentation process is the precise set of coordinates that represent the anatomical features in the scan. This representation of the anatomy allows definitive statements about the features to be made, for example, standard measurements such as size, length, volume, diameter, oblique cross-section and others. As a result, the shape and location of the anatomical feature or pathology may be calculated and incorporated into a personalized decision making process by the surgeon. These measurements may be used to drive critical decisions about the patient's condition and any proposed intervention.

More significantly the systems described herein can distinguish between normal and pathological states of the anatomy and any anatomical feature. The training process may be further embellished with this information and may use this to drive further classes of anatomical features. For example, blood may be identified and segmented within a medical scan. By incorporating information about the pathological state, blood clots also may be identified and segmented within a vessel such that the type and severity of the pathology may be identified. In combination with measurement data about the anatomy, this information is crucial for decision making in acute blood clot based pathologies such as stroke or coronary disease.

Pathology specific patentable artifacts may be created by combining the auto-segmentation algorithms described herein with large labeled training datasets that are specific to each pathology, such that the combination of the appropriate algorithm and the specific data creates unique sets of artifacts per pathology. The ability to provide specific grouping of functionalities of a segmentation provides significant benefits to specific clinical problems. Moreover, the ability to provide the automated segmentation also opens up a number of pathology specific applications that would benefit from the systems described herein.

In accordance with one aspect, a method for multi-schema analysis of patient specific anatomical features from medical images is provided. The method may include: receiving, by a server, medical images of a patient and metadata associated with the medical images indicative of a selected pathology; automatically processing, by the server, the medical images using a segmentation algorithm to label pixels of the medical images and to generate scores indicative of a likelihood that the pixels were labeled correctly; using, by the server, an anatomical feature identification algorithm to probabilistically match associated groups of the labeled pixels against an anatomical knowledge dataset to classify one or more patient specific anatomical features within the medical images; generating, by the server, a 3D surface mesh model defining a surface of the one or more classified patient specific anatomical features; extracting, by the server, information from the 3D surface mesh model based on the selected pathology; and generating, by the server, physiological information associated with the selected pathology for the 3D surface mesh model based on the extracted information. For example, the information extracted from the 3D surface mesh model may include a 3D surface mesh model of an anatomical feature isolated from the one or more classified patient specific anatomical features based on the selected pathology.

Generating, by the server, physiological information associated with the selected pathology for the 3D surface mesh model may include: determining start and end points of the isolated anatomical feature; taking slices at predefined intervals along an axis from the start point to the end point; calculating a cross-sectional area of each slice defined by a perimeter of the isolated anatomical feature; extrapolating a 3D volume between adjacent slices based on the respective cross-sectional areas; and calculating an overall 3D volume of the isolated anatomical feature based on the extrapolated 3D volumes between adjacent slices.

Generating, by the server, physiological information associated with the selected pathology for the 3D surface mesh model may include: determining start and end points of the isolated anatomical feature and a direction of travel from the start point to the end point; raycasting at predefined intervals along an axis in at least three directions perpendicular to the direction of travel and determining distances between intersections of each ray cast and the 3D surface mesh model; calculating a center point at each interval by triangulating the distances between intersections of each ray cast and the 3D surface mesh model; adjusting the direction of travel at each interval based on a directional vector between adjacent calculated center points, such that raycasting at the predefined intervals occur in at least three directions perpendicular to the adjusted direction of travel at each interval; and calculating a centerline of the isolated anatomical feature based on the calculated center points from the start point to the end point.

Generating, by the server, physiological information associated with the selected pathology for the 3D surface mesh model may include: calculating a centerline of the isolated anatomical feature; determining start and end points of the isolated anatomical feature and a directional vector from the start point to the end point; establishing cutting planes at predefined intervals along the centerline based on the directional vector from the start point to the end point, each cutting plane perpendicular to a direction of travel of the centerline at each interval; raycasting in the cutting plane at each interval to determine a position of intersection on the 3D surface mesh model from the centerline; and calculating a length across the 3D surface mesh model based on the determined positions of intersection at each interval.

Generating, by the server, physiological information associated with the selected pathology for the 3D surface mesh model may include: determining start and end points of the isolated anatomical feature; taking slices at predefined intervals along an axis from the start point to the end point; calculating a cross-sectional area of each slice defined by a perimeter of the isolated anatomical feature; and generating a heat map of the isolated anatomical feature based on the cross-sectional area of each slice.

Generating, by the server, physiological information associated with the selected pathology for the 3D surface mesh model may include: determining start and end points of the isolated anatomical feature; calculating a centerline of the isolated anatomical feature; determining a directional travel vector between adjacent points along the centerline; calculating a magnitude of change of directional travel vectors between adjacent points along the centerline; and generating a heat map of the isolated anatomical feature based on the magnitude of change of directional travel vectors between adjacent points along the centerline.

In some embodiments, the generated physiological information associated with the selected pathology for the 3D surface mesh model may include an associated timestamp, such that the method further includes: recording, by the server, the generated physiological information and the associated timestamp; and calculating, by the server, changes between the recorded physiological information over time based on associated timestamps, indicative of progression of the selected pathology. Accordingly, the method further may include: calculating, by the server, a magnitude of the changes between the recorded physiological information over time; and generating, by the server, a heat map of the isolated anatomical feature based on the magnitude of the changes between the recorded physiological information over time.

Extracting, by the server, information from the 3D surface mesh model based on the selected pathology may include: isolating an anatomical feature from the one or more classified patient specific anatomical features based on the selected pathology; analyzing features of the isolated anatomical feature with an anatomical feature database to identify one or more landmarks of the isolated anatomical feature; associating the one or more identified landmarks with the pixels of the medical images; and generating a 3D surface mesh model defining a surface of the isolated anatomical feature comprising the identified landmarks. Moreover, the method may further include: identifying, by the server, a guided trajectory for performing a surgical procedure from a surgical implement database based on the selected pathology and the one or more identified landmarks; and displaying the guided trajectory to a user.

In addition, the method further may include: receiving, by the server, patient demographic data; identifying, by the server, one or more medical devices from a medical device database based on the patient demographic data and the generated physiological information associated with the selected pathology for the 3D surface mesh model; and displaying the identified one or more medical devices to a user. Moreover, the method further may include: receiving, by the server, patient demographic data; identifying, by the server, one or more treatment options from a surgical implement database based on the patient demographic data and the generated physiological information associated with the selected pathology for the 3D surface mesh model; and displaying the identified one or more treatment options to a user.

Extracting, by the server, information from the 3D surface mesh model based on the selected pathology may include: isolating an anatomical feature from the one or more classified patient specific anatomical features based on the selected pathology; analyzing features of the isolated anatomical feature with an anatomical feature database to identify one or more landmarks of the isolated anatomical feature; analyzing features of the one or more landmarks with a reference fracture database to detect a fracture of the isolated anatomical feature; and generating a 3D surface mesh model of the isolated anatomical feature comprising the one or more identified landmarks and the detected fracture. Accordingly, the method further may include matching the 3D surface mesh model of the isolated anatomical feature against the reference fracture database to classify the detected fracture.

The method further may include: delineating, by the server, the classified one or more patient specific anatomical features into binary labels; separating, by the server, the binary labels into separate anatomical features; and mapping, by the server, the separate anatomical features to original grey scale values of the medical images and removing background within the medical images, and wherein the generated 3D surface mesh model defines a surface of the separate anatomical features, or comprises a volumetric render defined by mapping specific colors or transparency values to the classified one or more patient specific anatomical features. In some embodiments, the segmentation algorithm may include at least one of a threshold-based, decision tree, chained decision forest, or neural network method. The physiological information associated with the selected pathology may include at least one of diameter, volume, density, thickness, surface area, Hounsfield Unit standard deviation, or average.

In accordance with another aspect of the present disclosure, a system for multi-schema analysis of patient specific anatomical features from medical images is provided. The system may include a server and may: receive medical images of a patient and metadata associated with the medical images indicative of a selected pathology; automatically process the medical images using a segmentation algorithm to label pixels of the medical images and to generate scores indicative of a likelihood that the pixels were labeled correctly; use an anatomical feature identification algorithm to probabilistically match associated groups of the labeled pixels against an anatomical knowledge dataset to classify one or more patient specific anatomical features within the medical images; generate a 3D surface mesh model defining a surface of the one or more classified patient specific anatomical features; extract information from the 3D surface mesh model based on the selected pathology; and generate physiological information associated with the selected pathology for the 3D surface mesh model based on the extracted information. For example, the information extracted from the 3D surface mesh model may include a 3D surface mesh model of an anatomical feature isolated from the one or more classified patient specific anatomical features based on the selected pathology.

In accordance with yet another aspect of the present disclosure, a non-transitory computer-readable memory medium having instructions stored thereon is provided, that when loaded by at least one processor cause the at least one processor to: receive medical images of a patient and metadata associated with the medical images indicative of a selected pathology; automatically process the medical images using a segmentation algorithm to label pixels of the medical images and to generate scores indicative of a likelihood that the pixels were labeled correctly; use an anatomical feature identification algorithm to probabilistically match associated groups of the labeled pixels against an anatomical knowledge dataset to classify one or more patient specific anatomical features within the medical images; generate a 3D surface mesh model defining a surface of the one or more classified patient specific anatomical features; extract information from the 3D surface mesh model based on the selected pathology; and generate physiological information associated with the selected pathology for the 3D surface mesh model based on the extracted information.

BRIEF DESCRIPTION OF THE DRAWINGS

FIGS. 30A to 30E illustrate generating measurements of a patient specific anatomical feature in accordance with the principles of the present disclosure.

DETAILED DESCRIPTION

Figure 1:
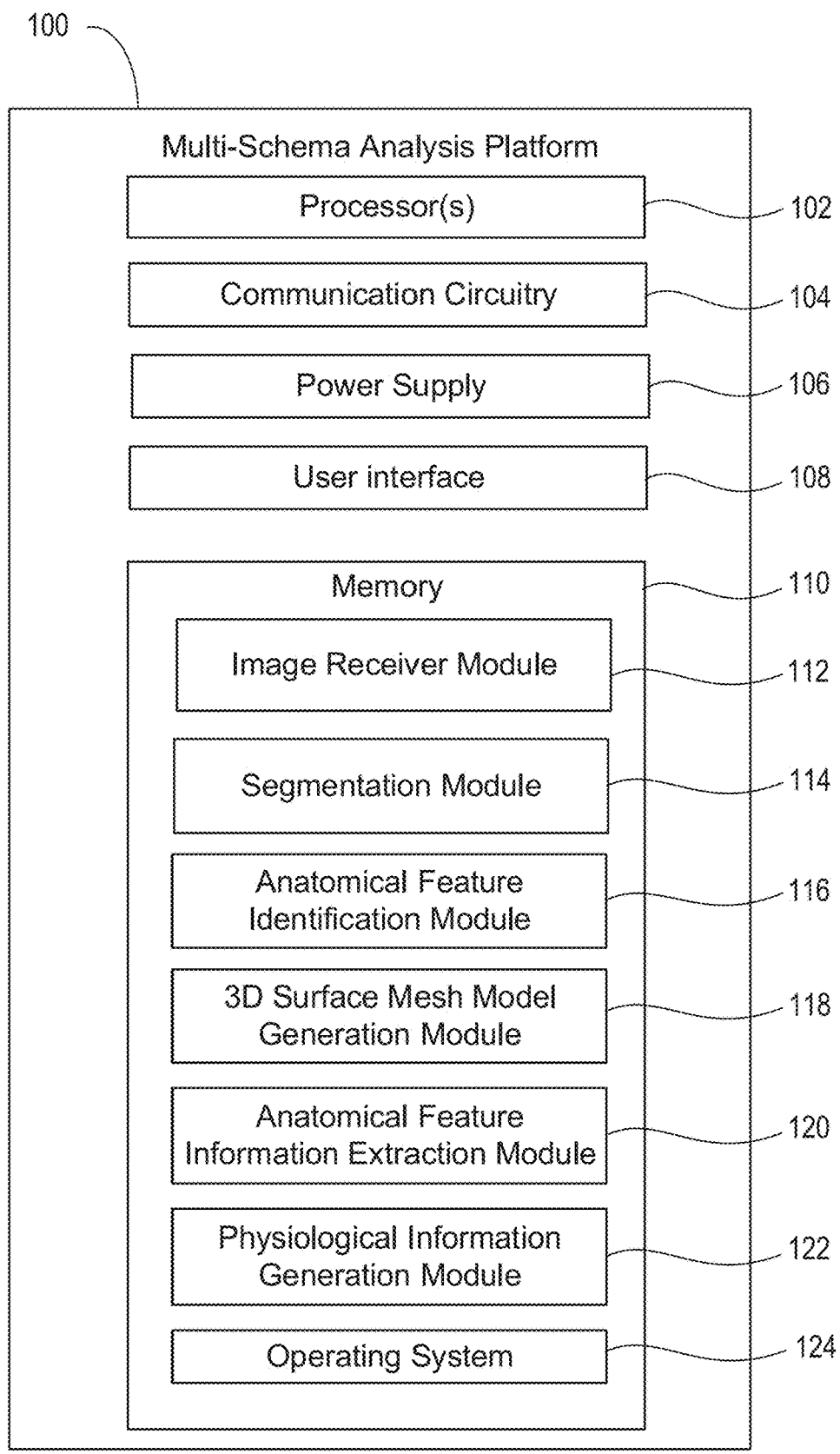
FIG. 1 shows some example components that may be included in an multi-schema analysis platform in accordance with the principles of the present disclosure.

Referring to FIG. 1, components that may be included in multi-schema analysis platform 100 are described. Platform 100 may include one or more processors 102, communication circuitry 104, power supply 106, user interface 108, and/or memory 110. One or more electrical components and/or circuits may perform some of or all the roles of the various components described herein. Although described separately, it is to be appreciated that electrical components need not be separate structural elements. For example, platform 100 and communication circuitry 104 may be embodied in a single chip. In addition, while platform 100 is described as having memory 110, a memory chip(s) may be separately provided.

Platform 100 may contain memory and/or be coupled, via one or more buses, to read information from, or write information to, memory. Memory 110 may include processor cache, including a multi-level hierarchical cache in which different levels have different capacities and access speeds. The memory may also include random access memory (RAM), other volatile storage devices, or non-volatile storage devices. Memory 110 may be RAM, ROM, Flash, other volatile storage devices or non-volatile storage devices, or other known memory, or some combination thereof, and preferably includes storage in which data may be selectively saved. For example, the storage devices can include, for example, hard drives, optical discs, flash memory, and Zip drives. Programmable instructions may be stored on memory 110 to execute algorithms for automatically segmenting and identifying patient specific anatomical features within medical images, including corresponding anatomical landmarks, generating 3D surface mesh models of the patient specific anatomical features, and extracting information from the 3D surface mesh models to generate physiological information of the patient specific anatomical features based on selected pathologies.

Platform 100 may incorporate processor 102, which may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. Platform 100 also may be implemented as a combination of computing devices, e.g., a combination of a DSP and a microprocessor, a plurality of microprocessors, one or more microprocessors in conjunction with a DSP core, or any other such configuration.

Platform 100, in conjunction with firmware/software stored in the memory may execute an operating system (e.g., operating system 124), such as, for example, Windows, Mac OS, Unix or Solaris 5.10. Platform 100 also executes software applications stored in the memory. For example, the software may be programs in any suitable programming language known to those skilled in the art, including, for example, C++, PHP, or Java.

Communication circuitry 104 may include circuitry that allows platform 100 to communicate with an image capture device and/or other computing devices for receiving image files, e.g., 2D medical images, and metadata associated therewith indicative of a patient specific pathology. Additionally or alternatively, image files may be directly uploaded to platform 100. Communication circuitry 104 may be configured for wired and/or wireless communication over a network such as the Internet, a telephone network, a Bluetooth network, and/or a WiFi network using techniques known in the art. Communication circuitry 104 may be a communication chip known in the art such as a Bluetooth chip and/or a WiFi chip. Communication circuitry 104 permits platform 100 to transfer information, such as 3D surface mesh models, physiological measurements, and treatment options, locally and/or to a remote location such as a server.

Power supply 106 may supply alternating current or direct current. In direct current embodiments, power supply may include a suitable battery such as a replaceable battery or rechargeable battery and apparatus may include circuitry for charging the rechargeable battery, and a detachable power cord. Power supply 106 may be charged by a charger via an inductive coil within the charger and inductive coil. Alternatively, power supply 106 may be a port to allow platform 100 to be plugged into a conventional wall socket, e.g., via a cord with an AC to DC power converter and/or a USB port, for powering components within platform 100.

User interface 108 may be used to receive inputs from, and/or provide outputs to, a user. For example, user interface 108 may include a touchscreen, display, switches, dials, lights, etc. Accordingly, user interface 108 may display information such as 3D surface mesh models, physiological measurements, heat maps, list of available medical devices for a patient specific pathology, treatment options, etc. to facilitate diagnosis, preoperative planning, and treatment for specific use cases, as described in further detail below. Moreover, user interface 108 may receive user input including patient demographic data, e.g., patient size, age, weight, medical history, patient specific pathologies, etc., and feedback from the user based on information displayed to the user, e.g., corrected anatomical feature identification, physiological measurements, specific anatomical feature selection, such that platform 100 may adjust the information accordingly. In some embodiments, user interface 108 is not present on platform 100, but is instead provided on a remote, external computing device communicatively connected to platform 100 via communication circuitry 104.

Memory 110, which is one example of a non-transitory computer-readable medium, may be used to store operating system (OS) 124, image receiver module 112, segmentation module 114, anatomical feature identification module 116, 3D surface mesh model generation module 118, anatomical feature information extraction module 120, and physiological information generation module 122. The modules are provided in the form of computer-executable instructions that may be executed by processor 102 for performing various operations in accordance with the disclosure.

Image receiver module 112 may be executed by processor 102 for receiving standard medical images, e.g., 2D and/or 3D medical images, of one or more patient specific anatomical features taken from one or a combination of the following: CT, MRI, PET, and/or SPCET scanner. The medical images may be formatted in a standard compliant manner such as with DICOM. The medical images may include metadata embedded therein indicative of a patient specific pathology associated with the patient specific anatomical features in the medical images. Image receiver module 112 may pre-process the medical images for further processing and analysis as described in further detail below. For example, the medical images may be pre-processed to generate a new set of medical images which are evenly distributed according to a predetermined orientation based on the patient specific anatomic feature, specific pathology of the patient, or any downstream application such as preoperative training and/or for machine learning/neural network training purposes. Moreover, image receiver module 112 may receive medical images taken simultaneously from multiple perspectives of a patient specific anatomical feature to enhance segmentation of the patient specific anatomical features.

Segmentation module 114 may be executed by processor 102 for automated segmentation of the medical images received by image receiver module 112, e.g., to assign a label to each pixel of the medical images. The assigned label may represent a specific tissue type, e.g., bone, soft tissue, blood vessel, organ, etc. Specifically, segmentation module 114 may use machine learning based image segmentation techniques including one or a combination of the following techniques: threshold-based, decision tree, chained decision forest, or a neural network method, such that the results of each technique may be combined to produce a final segmentation result, as described in U.S. Pat. No. 11,138,790 and U.S. Patent Appl. Pub. No. 2021/0335041 to Haslam, both assigned to the assignee of the present disclosure, and both incorporated herein in their entireties by reference. The machine learning based image segmentation techniques may be trained using a knowledge database including pre-labeled medical images (i.e., ground truth data).

For example, segmentation module 114 may apply a first segmentation technique, e.g., a threshold-based segmentation, to assign a label to each pixel of the medical images based on whether a characteristic, e.g., Hounsfield value, of the pixel meets/exceeds a predetermined threshold. The predetermined threshold may be determined via, e.g., histogram analysis, as described in U.S. Pat. No. 11,138,790. Segmentation module 114 further may expand on the threshold-based segmentation technique by using a logistic or probabilistic function to calculate a score as to the likelihood of a pixel being the tissue type as labeled by the threshold-based segmentation.

Segmentation module 114 may then apply a decision tree to each labeled pixel of the medical images to thereby classify/label each pixel based at least in part on, but not solely on, the score. As described in U.S. Pat. No. 11,138,790, the decision tree may be applied to a subset of the labeled pixels by subsampling the medical images, such that segmentation module 114 may recover full segmentation of the medical images by using standard interpolation methods to up-scale the labeled pixels of the subset of pixels of the medical images. The decision tree may consider, for each pixel, the score as well as, for example, the following properties: how many pixels looking almost like bone are near the pixel in question; how many pixels looking exactly like bone are near the pixel in question; or how strong is an overall gradient of the image at the given pixel. For example, if a pixel in question is labeled as bone with a score of 60/100, the first decision node of the decision tree can ask how many pixels looking almost like bone are near the pixel in question. If the answer is close to zero, meaning that very few pixels near the pixel in question look almost like bone, segmentation module 114 may determine that the pixel in question is not bone, even though the previous bone label had a score of 60/100. A new score may then be generated as to the likelihood that the pixel in question was correctly labeled by the decision tree algorithm. Accordingly, applying the decision tree to the pixels of the medical images may produce more accurate final segmentation results with less noise. As will be understood by a person having ordinary skill in the art, the decision tree may consider other properties that may be useful in determining a label for the pixel.

Additionally or alternatively, segmentation module 114 may apply a chained decision forest, in which the results of an initial/previous decision tree and the results of another segmentation technique, e.g., a Neural Network, for the same pixel in question may be fed to a new decision tree along with the scores associated with the results. For example, the new decision tree may ask one or more questions as described above to determine whether each of the previous segmentation techniques correctly labeled the pixel in question. Thus, if the initial/previous decision tree labeled the pixel in question as bone; whereas, the Neural Network labeled the pixel in question as not bone, the new decision tree may determine that the pixel in question is bone based on the responses to the one or more questions asked by the chained decision forest, such that the label allocated by the Neural Network for the pixel in question is discarded. Moreover, each forest-node may be treated as a simple classifier that produces a score as to how likely the pixel was correctly labeled by each subsequent new decision tree. Accordingly, applying the chained decision forest to the pixels of the medical images may produce more accurate final segmentation results.

Anatomical feature identification module 116 may be executed by processor 102 for identifying one or more patient specific anatomical features within the medical images by probabilistically matching the pixels labeled by segmentation module 114 against an anatomical knowledge dataset within the knowledge database. Specifically, as described in U.S. Pat. No. 11,138,790, anatomical feature identification module 116 initially may group the pixels labeled by segmentation module 114, e.g., by establishing links between the different labeled/classified pixels based on similarities between the labeled pixels. For example, all the pixels labeled "bone" may be grouped/linked together in a first group, all the pixels labeled "organ" may be grouped/linked together in a second group, and all the pixels labeled "blood vessel" may be grouped/linked together a third group.

Anatomical feature identification module 116 may then use an anatomical feature identification algorithm to explore the anatomical knowledge dataset to identify the patient specific anatomical features within the medical images by establishing links between the grouped labeled pixels with existing knowledge within the anatomical knowledge dataset. For example, the existing knowledge may include known information regarding various anatomic features such as tissue types, e.g., bone, blood vessel, or organ, etc., represented as nodes within a graph database of the anatomical knowledge dataset, as well as pre-labeled ground truth data that may be used to train the various segmentation algorithms.

The medical ontology of the existing knowledge of anatomic features within the graph database may be represented as a series of nodes which are grouped together through at least one of: functions, proximity, anatomical groupings, or frequency of appearance in the same medical image scan. For example, nodes representing an organ may be grouped together as a heart because they are within a predetermined proximity to each other, are all near nodes representing a blood vessel which are grouped together as an aorta, and have a high frequency of appearance in the same medical image scan. Accordingly, the anatomical feature identification algorithm may identify the patient specific anatomical feature within the medical image through exploration of the graph database to determine which group of nodes most resemble the grouped labeled pixels, e.g., based on the established links between the grouped labeled pixels and the group of nodes. Anatomical feature identification module 116 further may generate a score representing the likelihood that the patient specific anatomical feature was correctly identified by the anatomical feature identification algorithm.

3D surface mesh model generation module 118 may be executed by processor 102 for generating a 3D surface mesh model of the patient specific anatomical features within the medical images based on the results of the segmentation algorithm as well as the results of the anatomical feature identification algorithm, described above, and for extracting a 3D surface mesh model from the scalar volumes to generate a 3D printable model. For example, as described in U.S. Pat. No. 11,138,790, the 3D surface mesh model may have the following properties: all disjointed surfaces are closed manifolds, appropriate supports are used to keep the disjointed surfaces/volumes in place, appropriate supports are used to facilitate 3D printing, and/or no surface volumes are hollow, such that the 3D surface mesh model is 3D printable. Moreover, 3D surface mesh model generation module 118 may generate 3D surface mesh models of the patient specific anatomical features including any corresponding landmarks of the anatomical features, as described in further detail below.

Anatomical feature information extraction module 120 may be executed by processor 102 for extracting information from the 3D surface mesh model generated by 3D surface mesh model generation module 118. For example, anatomical feature information extraction module 120 may extract one or more specific anatomical features from the 3D surface mesh model representing the patient specific anatomical features within the medical images, based on the selected pathology indicated in the metadata received by image receiver module 112. Alternatively, platform 100 may receive information indicative of a selected pathology associated with the medical images directly from the user via user interface 108, e.g., along with patient demographic data and medical history. Accordingly, if a specific pathology is known for a given patient, anatomical feature information extraction module 120 may automatically extract the 3D surface mesh model of the specific anatomical feature including the pathology from the 3D surface mesh model generated by 3D surface mesh model generation module 118.

Physiological information generation module 122 may be executed by processor 102 for generating physiological information associated with the selected pathology for the 3D surface mesh model based on the information extracted by anatomical feature information extraction module 120. For example, based on the selected pathology, physiological information generation module 122 may perform calculations to determine physiological measurements relevant to the diagnosis and/or treatment of the pathology, e.g., by providing a list of medical devices appropriate to treat the pathology and/or treatment options based on measurements of the anatomical feature and patient demographic data. The list of medical devices and/or treatment options may be extracted from a medical device database or a surgical implement database by physiological information generation module 122. As described in further detail below with reference to FIGS. 3A to 24F, the physiological measurements associated with the selected pathologies determined by physiological information generation module 122 may include, but are not limited to, volume, cross-sectional area, diameter, centerline, surface, density, thickness, tortuosity, fracture size and location, blood clots, occlusions, and rate of growth over time of the anatomical feature and/or corresponding landmark. Moreover, physiological information generated by physiological information generation module 122 may be used to generate heat maps to facilitate visual observation of the physiological measurements of the patient specific anatomical feature.

Figure 2:
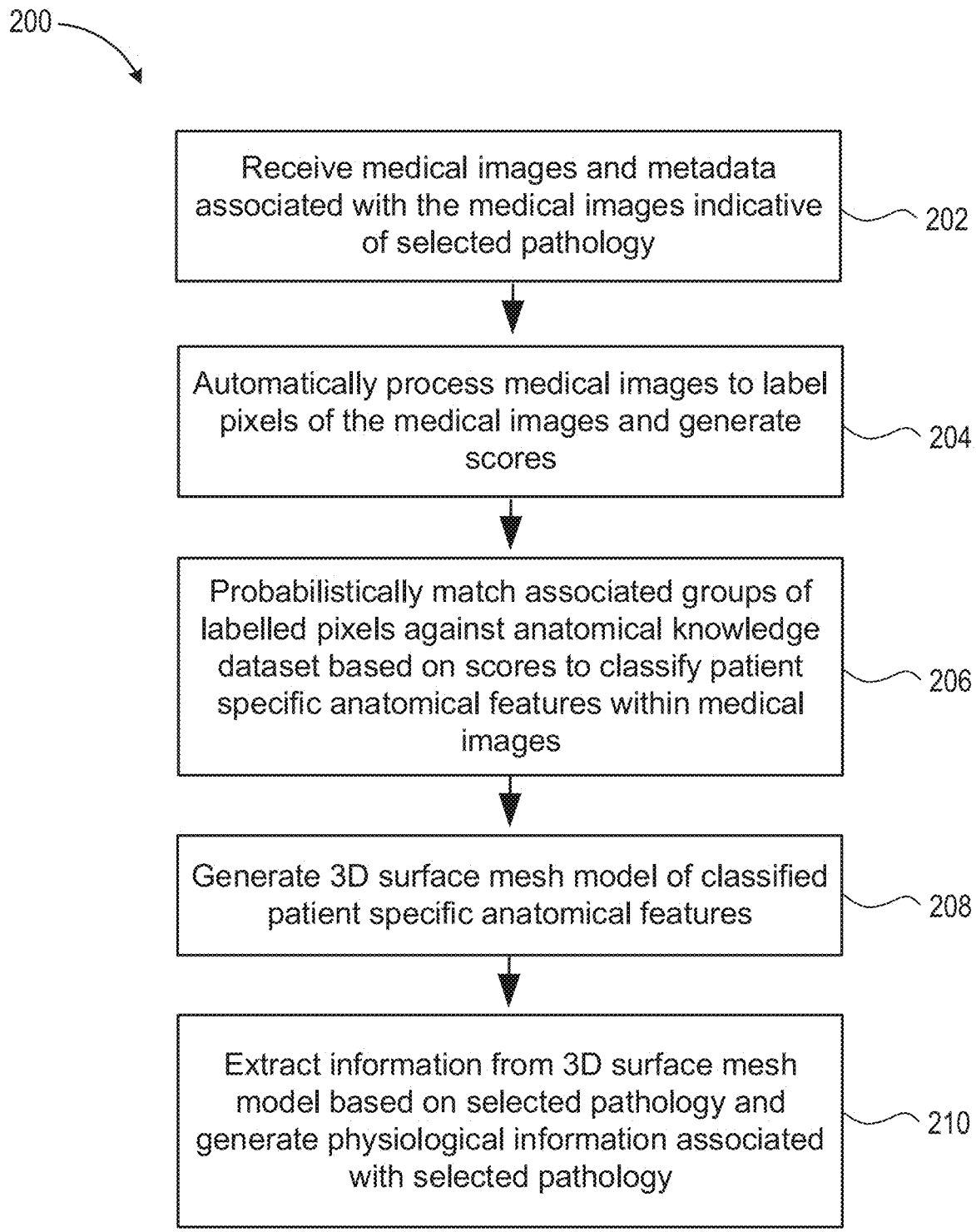
FIG. 2 is a flow chart illustrating exemplary method steps for multi-schema analysis of patient specific anatomical features from medical images in accordance with the principles of the present disclosure.

Referring now to FIG. 2, exemplary method 200 for multi-schema analysis of patient specific anatomical features from medical images using platform 100 is provided. At step 202, medical images and metadata associated with the medical images indicative of a selected pathology may be received image receiver module 112. As described above, information indicative of the selected pathology may be directly received via user input along with patient demographic data. At step 204, segmentation module 114 may automatically process the medical images using a segmentation algorithm to label pixels of the medical images and to generate scores indicative of a likelihood that the pixels were labeled correctly. For example, the segmentation algorithm may use one or a combination of various machine learning based image segmentation techniques, trained with a knowledge dataset of pre-labeled medical images, to label pixels of the medical images.

At step 206, anatomical feature identification module 116 may group together pixels labeled at step 204 based on similarities, and use an anatomical feature identification algorithm to probabilistically match associated groups of the labeled pixels against an anatomical knowledge dataset to classify one or more patient specific anatomical features within the medical images. At step 208, 3D surface mesh model generation module 118 may generate a 3D surface mesh model defining a surface of the one or more classified patient specific anatomical features within the medical images. At step 210, anatomical feature information extraction module 120 may extract information from the 3D surface mesh model based on the selected pathology, and physiological information generation module 122 may generate physiological information associated with the selected pathology for the 3D surface mesh model based on the extracted information. The physiological information generated is described in further detail below with reference to FIGS. 3A to 24F.

Figure 3:
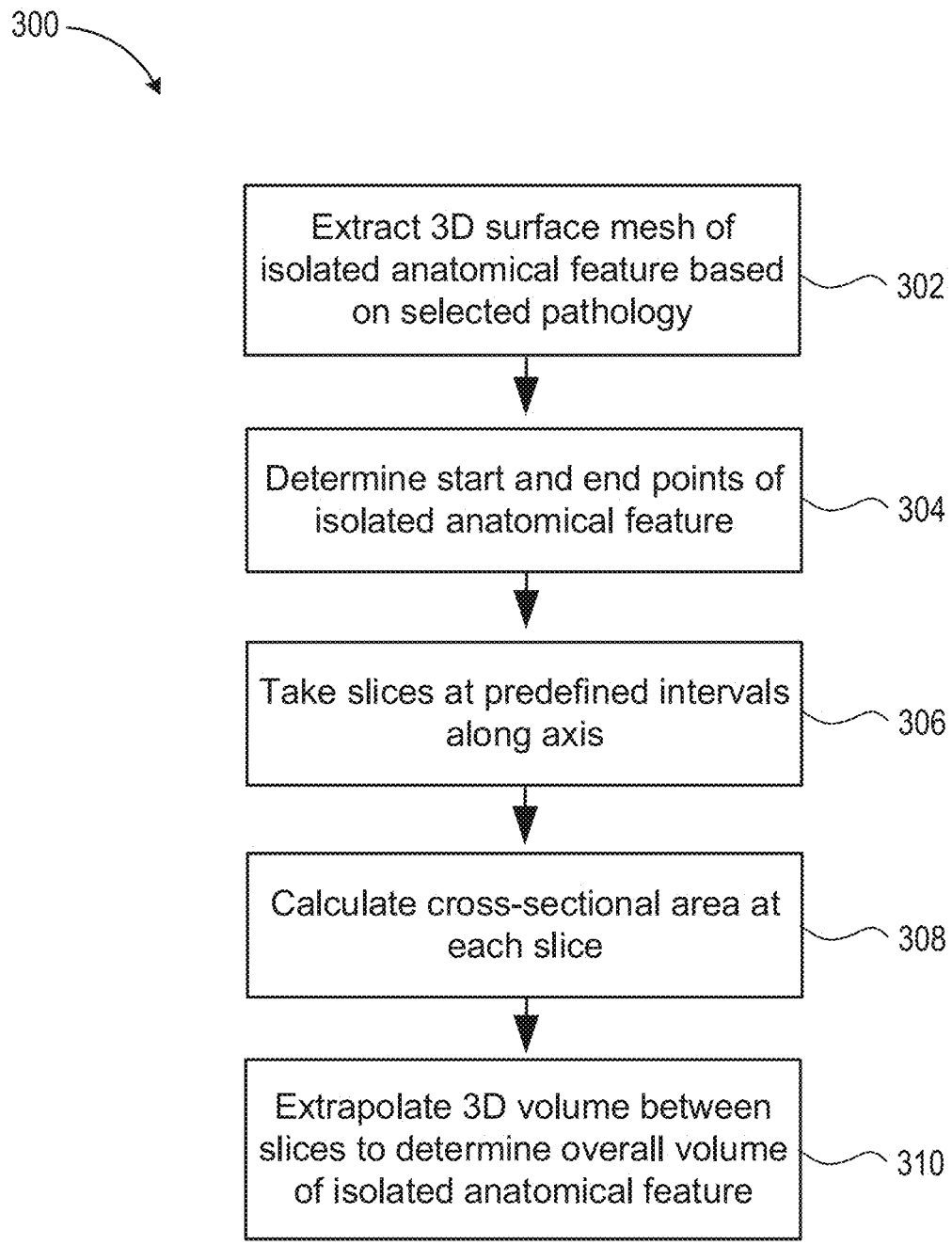
FIG. 3 is a flow chart illustrating exemplary method steps for generating volume measurements of a patient specific anatomical feature in accordance with the principles of the present disclosure.

Referring now to FIG. 3, exemplary method 300 for generating volume measurements of a patient specific anatomical feature is provided. As described above with regard to step 210 of method 200 for multi-schema analysis of patient specific anatomical features from medical images of FIG. 2, physiological information, e.g., volume measurements of the patient specific anatomical feature associated with the selected pathology, may be generated from the generated 3D surface mesh model. For example, at step 302, a specific anatomical feature may be isolated from the patient specific anatomical features within the medical images based on the selected pathology, e.g., as indicated by the metadata associated with the medical images, for further analysis, such that a 3D surface mesh model of the isolated anatomical feature may be extracted from the 3D surface mesh model of the patient specific anatomical features and recorded. Accordingly, only the anatomical feature(s) comprising the pathology may be further analyzed to generate physiological information associated with the pathology.

At step 304, a start point and an end point of the isolated anatomical feature is determined, e.g., at opposite ends of the isolated anatomical feature. For example, the start and end points may be determined via a machine learning algorithm that explores the anatomical knowledge dataset to derive the start and end points of the isolated anatomical feature. At step 306, a predetermined step size may be determined, such that slices may be taken at regular intervals defined by the predetermined step size along an axis of the isolated anatomical feature. For example, the axis may the centerline of the isolated anatomical feature determined based on a directional vector extending from the start point to the end point, as described in further detail below. Accordingly, a slice of the isolated anatomical feature may be taken at each interval perpendicular to the direction of travel along the centerline, beginning from the start point and in the direction of the end point.

Figure 4A:
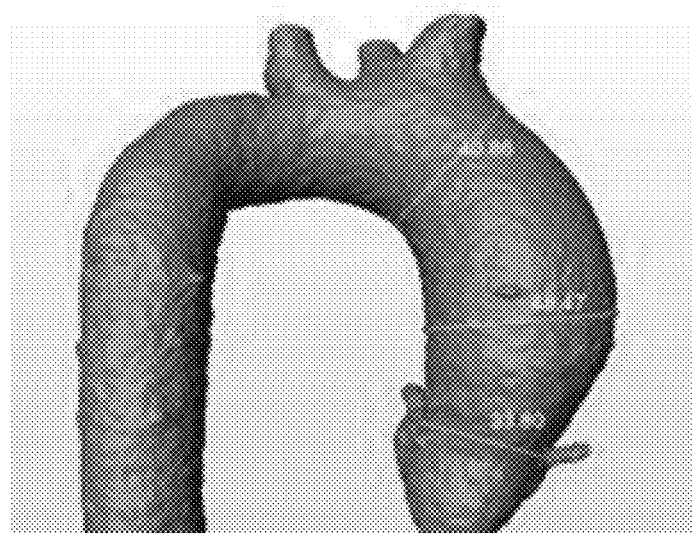
FIG. 4A illustrates cross-sectional area measurements at various points along a vessel.
Figure 4B:
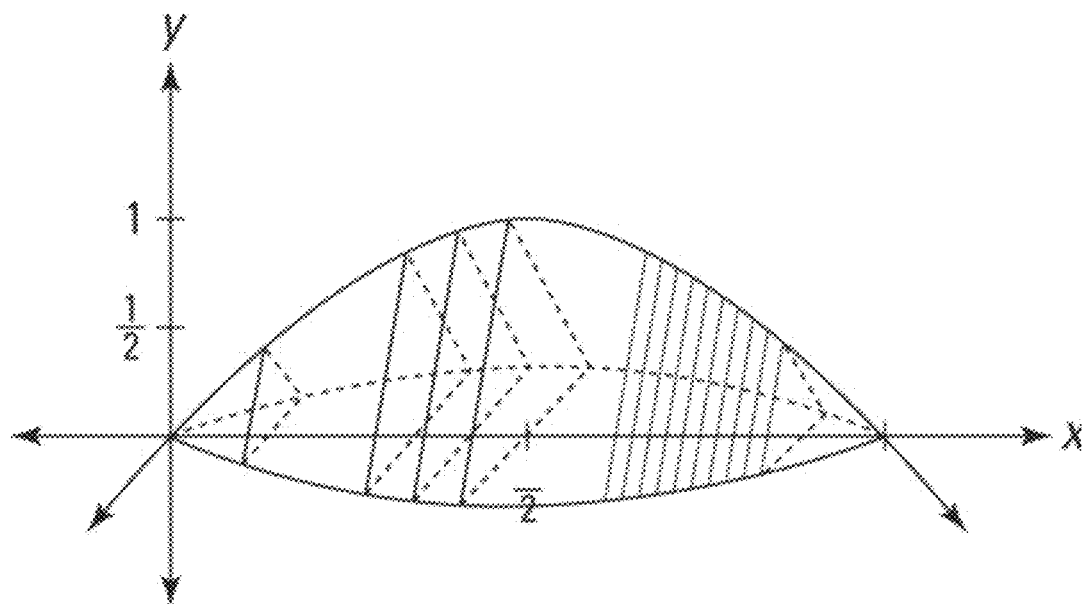
FIG. 4B illustrates determination of volume based on the cross-sectional area measurements in accordance with the principles of the present disclosure.

At step 308, using standard computational functions, the cross-sectional area at each slice of the isolated anatomical feature may be calculated, as defined by the perimeter of the isolated anatomical feature, as shown in FIG. 4A. For example, the cross-sectional area of the automatically segmented labels for specific portions of anatomy, e.g., the mitral or aortic valve anatomy, may be calculated based on a derivative of the largest two cross sections of the anatomy, e.g., using $A \times B \times \pi$. In the case of an aneurysm, this data may be used to provide surgeons a neck-to-dome ratio automatically for the anatomy. FIG. 4A illustrates three slices along an isolated anatomical feature, e.g., an aorta when the associated pathology is an aneurysm, for which cross-sectional areas have been calculated and displayed over the 3D surface mesh model of the aorta. FIG. 4B illustratively shows how slices may be taken along an axis of a complex structure for purposes of calculating cross-sectional areas thereof.

Referring again to FIG. 3, at step 310, the 3D volume between each adjacent slices may be extrapolated based on the cross-sectional areas of the isolated anatomical feature at adjacent slices, such that the overall volume of the isolated anatomical structure may be determined based on the extrapolated 3D volumes, e.g., by taking the sum of the extrapolated 3D volumes. Alternatively, the volume of the automatically segmented labels for specific portions of an isolated anatomical feature, e.g., the left atrial appendage of the heart, may be calculated based on the number of voxels within the semantically labeled portion of anatomy, such that the volume may be displayed to the user for assessment.

Figure 5:
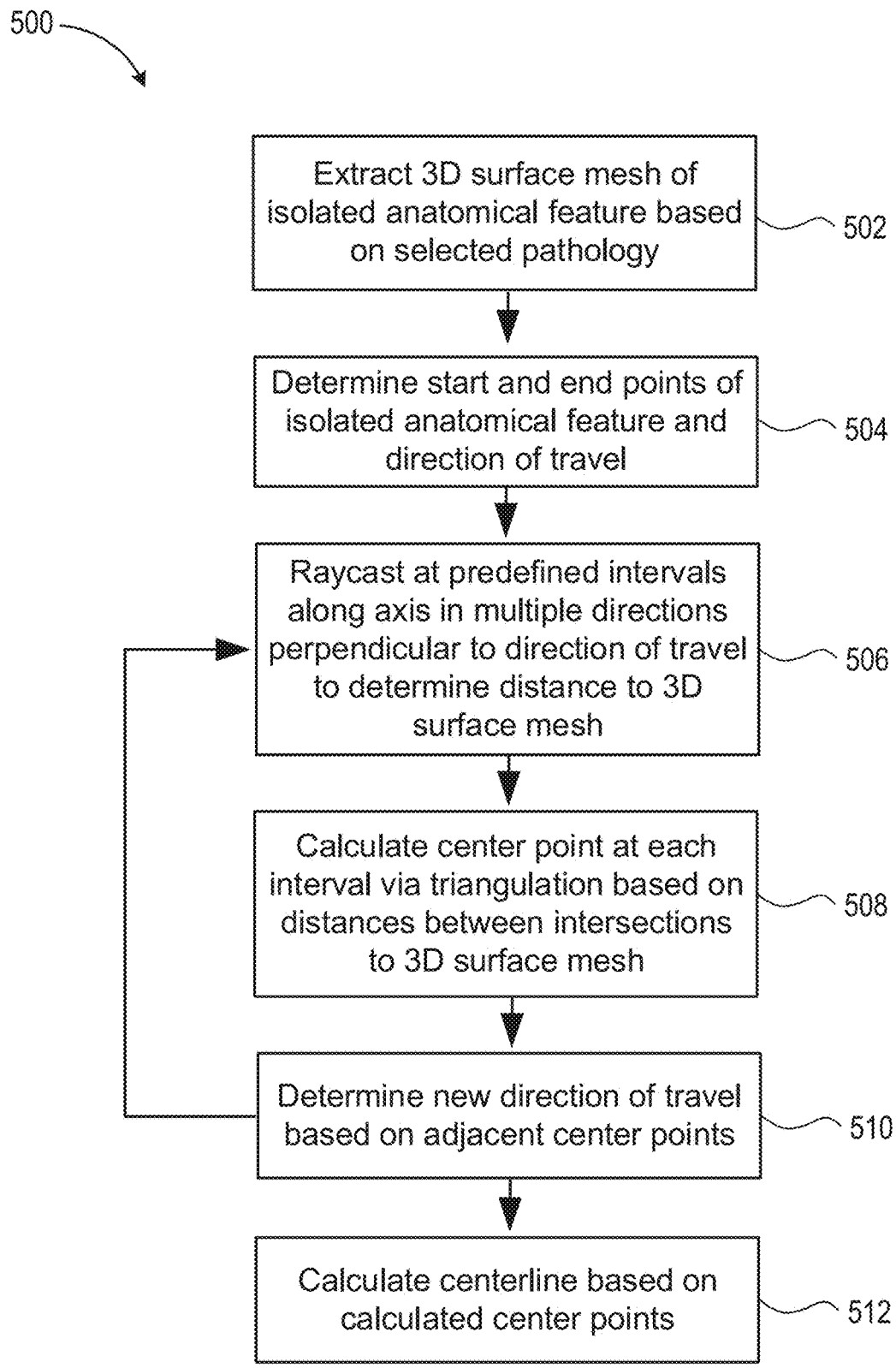
FIG. 5 is a flow chart illustrating exemplary method steps for generating centerline measurements of a patient specific anatomical feature in accordance with the principles of the present disclosure.

Referring now to FIG. 5, exemplary method 500 for generating centerline measurements of a patient specific anatomical feature is provided. As described above with regard to step 210 of method 200 for multi-schema analysis of patient specific anatomical features from medical images of FIG. 2, physiological information, e.g., centerline measurements of the patient specific anatomical feature associated with the selected pathology, may be generated from the generated 3D surface mesh model. For example, at step 502, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded.

At step 504, a start point and an end point of the isolated anatomical feature is determined, e.g., at opposite ends of the isolated anatomical feature, such that a directional vector may be determined that extends from the start point toward to end point. For example, the start and end points may be determined via a machine learning algorithm that explores the anatomical knowledge dataset to derive the start and end points of the isolated anatomical feature. The start and end points further may be close to a bounding box of the 3D surface mesh model, and on a common plane. Moreover, an initial direction of travel may be determined consistent with the directional vector extending from the start point to the end point.

Figure 6:
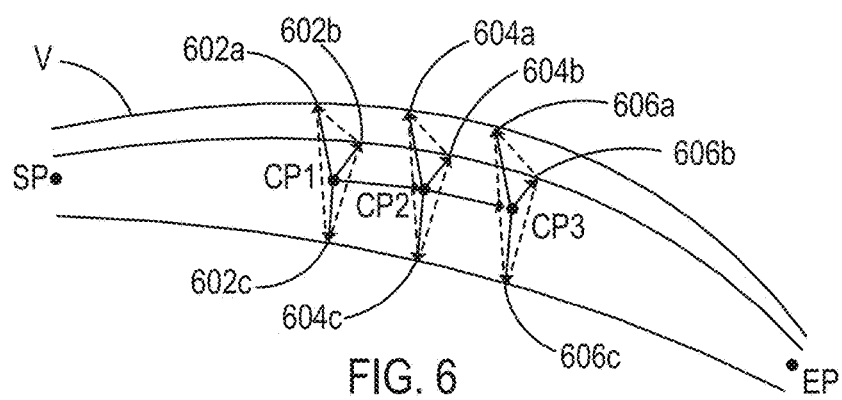
FIG. 6 illustrates determination of a centerline in accordance with the principles of the present disclosure.

At step 506, a predetermined step size may be determined, such that a cutting plane may be established at regular intervals defined by the predetermined step size along an axis of the isolated anatomical feature. The cutting plane at each interval may be perpendicular to the direction of travel associated with the interval. For example, the initial cutting plane may be perpendicular to the initial direction of travel based on the directional vector extending from the start point to the end point. Moreover, multiple rays, e.g., three rays, may be raycast in multiple predefined directions along the cutting plane at each interval, perpendicular to the direction of travel and radially outwardly toward the perimeter of the isolated anatomical feature, such that the position of the intersections of the rays cast and the 3D surface mesh model may be determined. For example, as shown in FIG. 6, in a direction of travel from start point SP toward end point EP, the first set of three rays cast may intersect the 3D surface mesh model of the isolated anatomical feature, e.g., vessel V, at points 602a, 602b, 602c. At step 506, if the point from which the rays are cast are determined to be outside of the 3D surface mesh model, the point may be moved to within the 3D surface mesh model.

At step 508, the center point, e.g., CP1, of the isolated anatomical feature within the cutting plane at each interval may be determined, e.g., by triangulating the distances between each of the intersection points, e.g., points 602a, 602b, 602c, of the isolated anatomical feature. At step 510, a new direction of travel may be determined at each interval based on a directional vector extending from the previous center point of the previous interval and the current center point. For example, in FIG. 6, the new direction of travel at the first interval may be consistent with a directional vector extending from start point SP to center point CP1. If the isolated anatomical feature is a branched vessel, steps 506 to 510 may be repeated through both branches of the vessel, thereby generating a centerline for each branch of the 3D surface mesh model of the vessel.

Figure 7A:
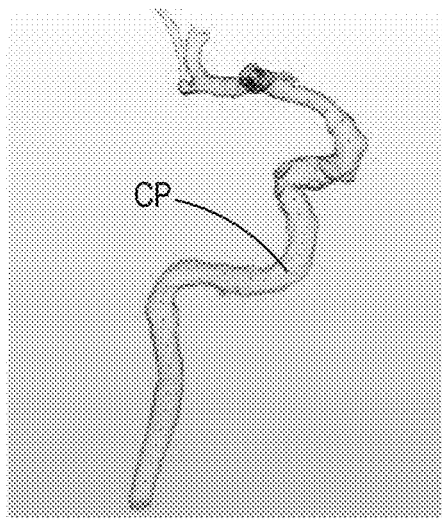
FIG. 7A illustrates center points of a vessel.

Method 500 may repeat steps 506 to 510 until end point EP is reached. For example, as shown in FIG. 6, at the second interval, three rays may be cast along a cutting plane perpendicular to the direction of travel that is defined by the directional vector extending from start point SP to center point CP1. The distances between intersection points 604a, 604b, 604c of the rays cast and the 3D surface mesh model may be triangulated to determine center point CP2 at the second interval. The previous direction of travel may then be adjusted to a new direction of travel defined by the directional vector extending from center point CP1 to center point CP2. Similarly, at the third interval, three rays may be cast along a cutting plane perpendicular to the direction of travel that is defined by the directional vector extending from center point CP1 to center point CP2. The distances between intersection points 606a, 606b, 606c of the rays cast and the 3D surface mesh model may be triangulated to determine center point CP3 at the third interval. The previous direction of travel may then be adjusted to a new direction of travel defined by the directional vector extending from center point CP2 to center point CP3. As described above, steps 510 to 512 may be repeated until end point EP is reached to thereby determine a series of center points CP along an axis of the isolated anatomical feature, as shown in FIG. 7A. Accordingly, as described above, the point from which the rays are cast will be outside of the 3D surface mesh model beyond end point EP, such that the point cannot be returned to within the 3D surface mesh model, thereby indicating an end of the centerline of the isolated anatomical feature.

Figure 7B:
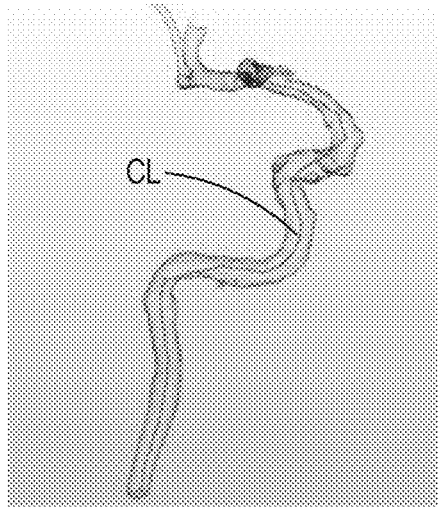
FIG. 7B illustrates a centerline of the vessel.
Figure 7C:
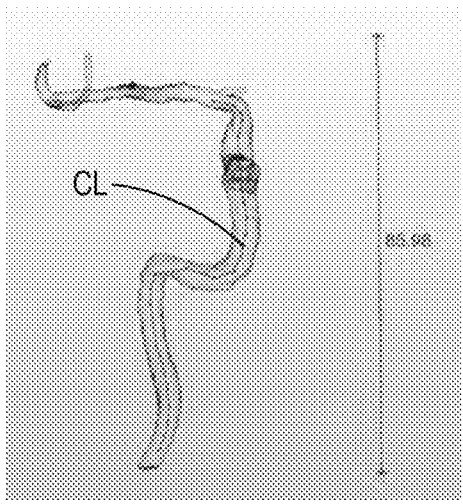
FIG. 7C illustrates measurement of length of the centerline of the vessel.
Figure 7D:
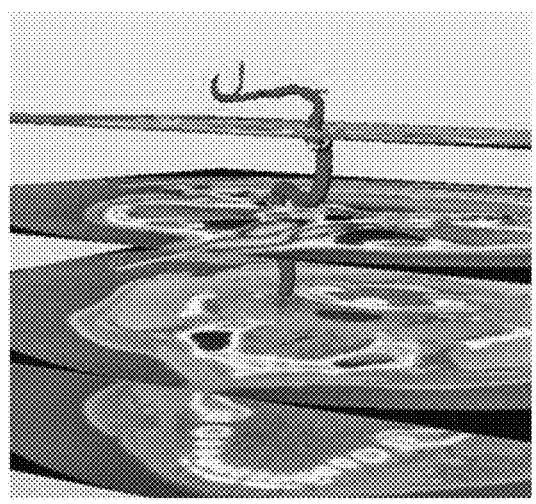
FIG. 7D illustrates the vessel depicted across medical images.
Figure 8A:
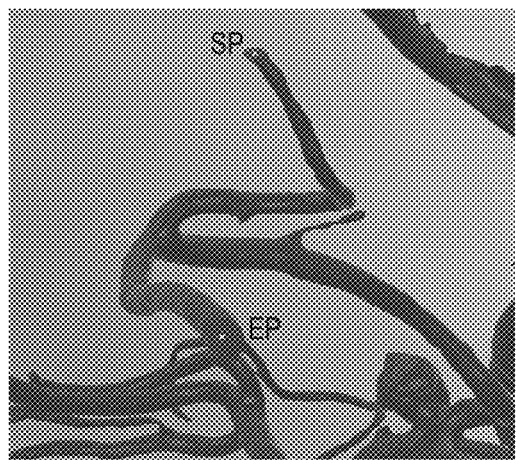
FIG. 8A illustrates start and end points of a patient specific anatomical feature.
Figure 8B:
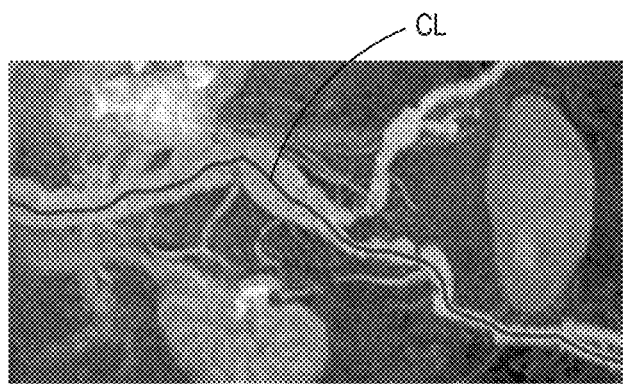
FIG. 8B illustrates a centerline of the patient specific anatomical feature.
Figure 8C:
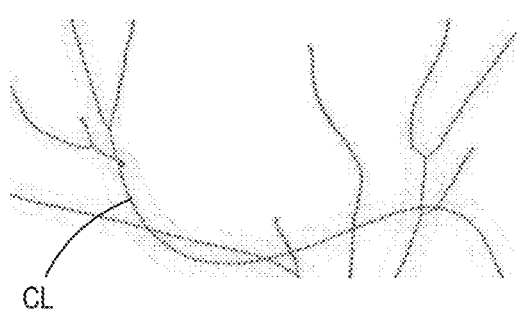
FIG. 8C illustrates the centerlines of various patient specific anatomical features.
Figure 8D:
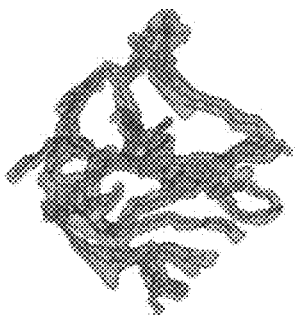
FIG. 8D illustrates the centerlines of a network of patient specific anatomical features.

At step 512, the centerline of the isolated anatomical feature may be determined based on the totality of center points, e.g., CP1, CP2, CP3 . . . CPn. For example, the centerline may be a line drawn through all of the calculated center points of the isolated anatomical feature, as shown in FIG. 6. FIG. 7B illustrates centerline CL of an isolated anatomical feature as a line drawn through all of center points CP of FIG. 7A. Accordingly, as shown in FIG. 7C, the overall length of centerline CL of the isolated anatomical feature may be determined. FIG. 7D illustrates the 3D surface mesh model of the isolated anatomical feature of FIGS. 7A to 7C across the original medical images.

Referring now to FIG. 8, method 500 may be used to determine the centerlines of a vast network of patient specific anatomical features. For example, FIG. 8A illustrates the start and end points determined for a 3D surface mesh model of an isolated anatomical feature. FIG. 8B illustrates centerline CL determined for an isolated anatomical feature mapped to the original medical image. FIG. 8C illustrates centerlines CL for an anatomical feature comprising a plurality of vessels, and FIG. 8D illustrates centerlines CL for an anatomical feature comprising a vast network of vessels.

Figure 9:
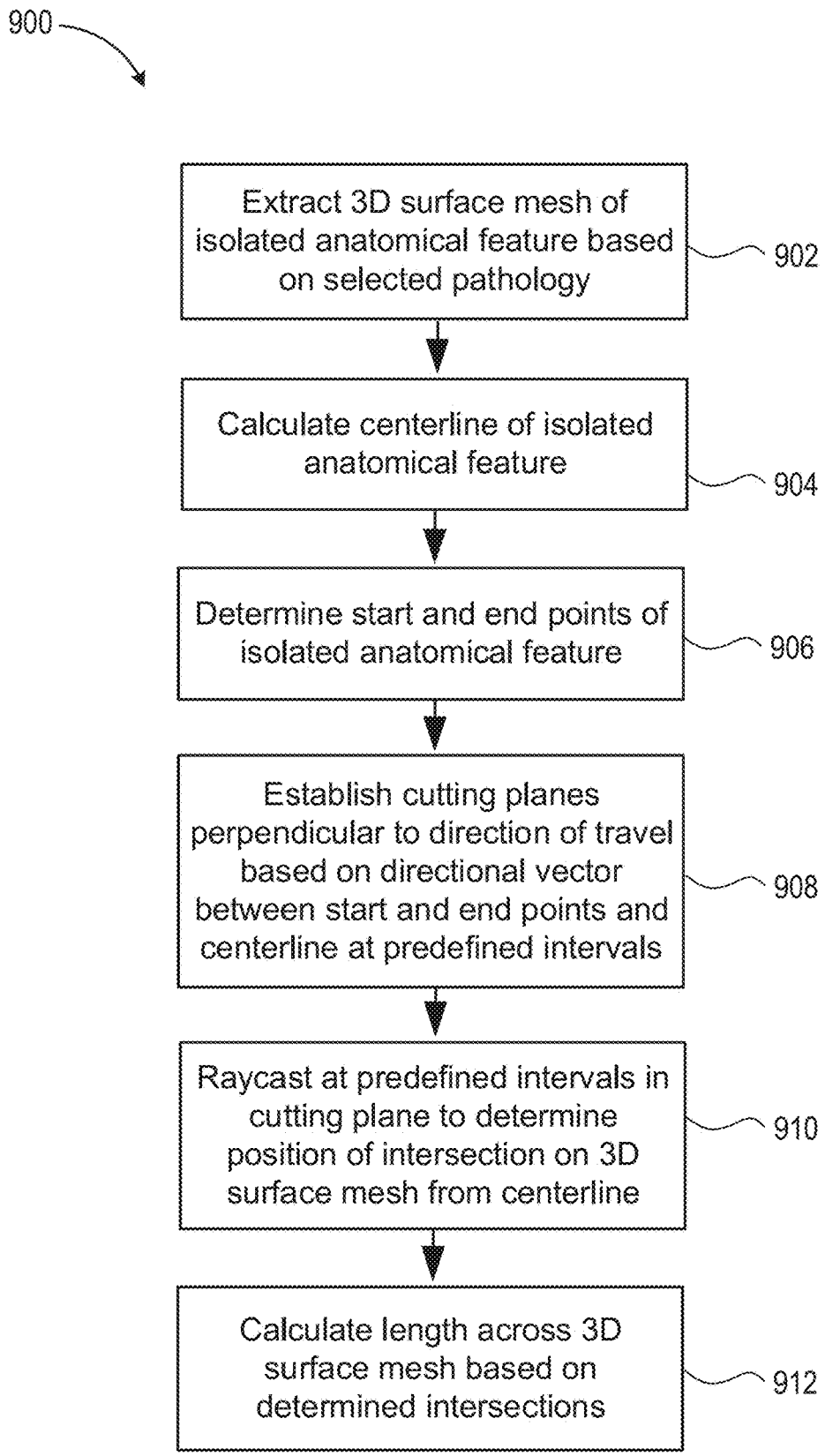
FIG. 9 is a flow chart illustrating exemplary method steps for generating surface length measurements of a patient specific anatomical feature in accordance with the principles of the present disclosure.

Referring now to FIG. 9, exemplary method 900 for generating surface length measurements of a patient specific anatomical feature is provided. As described above with regard to step 210 of method 200 for multi-schema analysis of patient specific anatomical features from medical images of FIG. 2, physiological information, e.g., surface length measurements of the patient specific anatomical feature associated with the selected pathology, may be generated from the generated 3D surface mesh model. For example, at step 902, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded.

Figure 10:
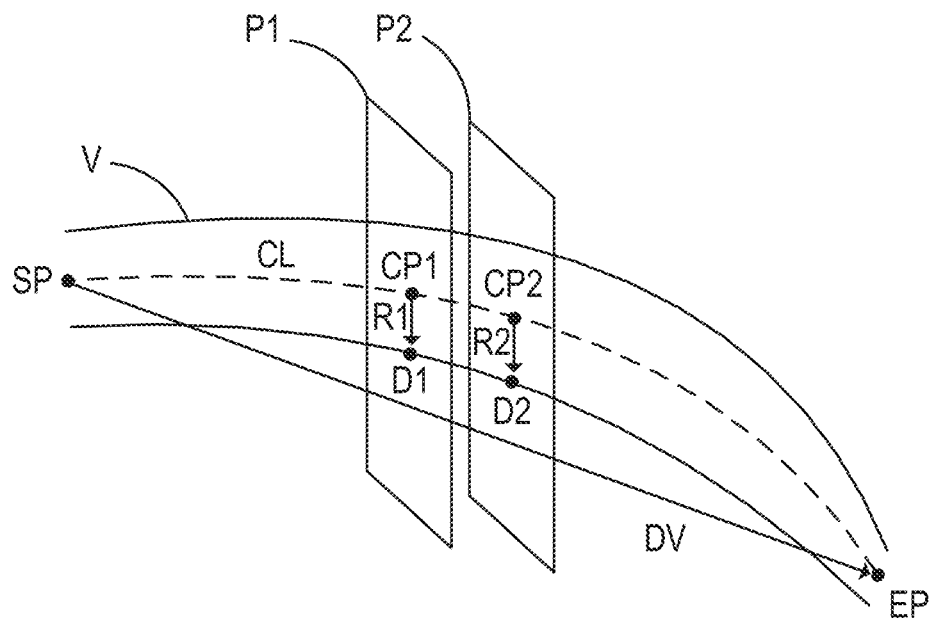
FIG. 10 illustrates determination of a surface length in accordance with the principles of the present disclosure.

At step 904, the centerline of the isolated anatomical feature may be determined, e.g., via method 500 described above. At step 906, a start point and an end point of the isolated anatomical feature may be determined, e.g., at opposite ends of the isolated anatomical feature. At step 908, a predetermined step size may be determined, such that a cutting plane may be established at regular intervals defined by the predetermined step size along an axis of the isolated anatomical feature. As shown in FIG. 10, the cutting planes, e.g., P1, P2, at each interval of the isolated anatomical feature, e.g., vessel V, may be perpendicular to the direction of travel associated with the interval, e.g., the direction of travel of the centerline at the interval as described above, and may include the center point along centerline CL, e.g., CP1, CP2, at the respective interval and a point along directional vector DV extending from start point SP to end point EP.

Figure 11:
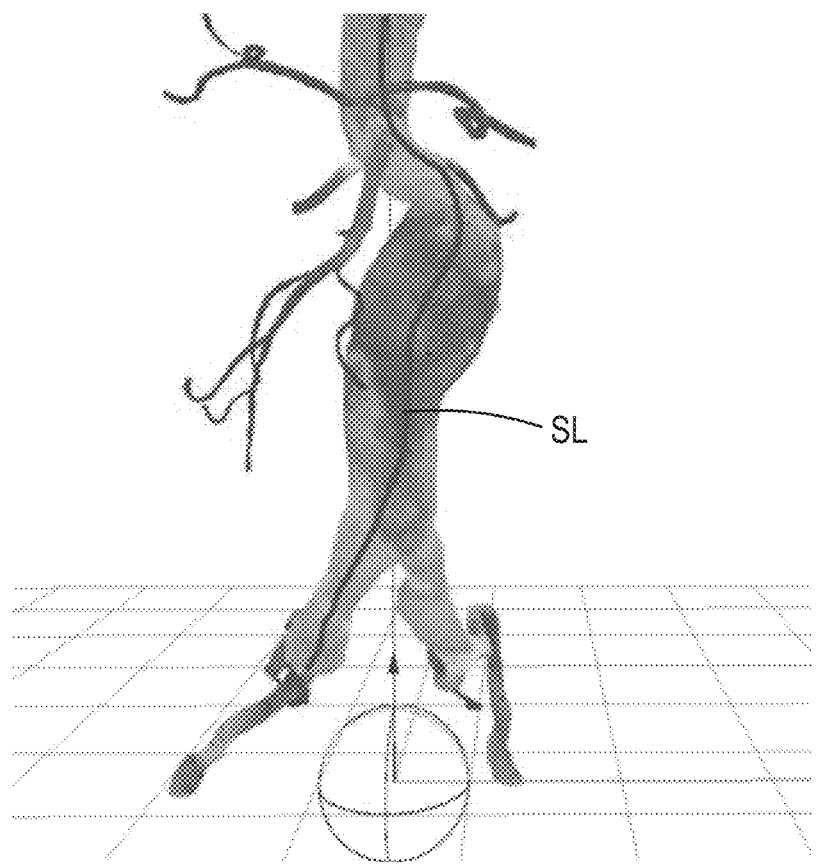
FIG. 11 illustrates a surface length of a patient specific anatomical feature.

At step 910, a ray, e.g., rays R1, R2, may be cast along each cutting plane, e.g., cutting plane P1, P2, at each interval from the respective center point, e.g., center points CP1, CP2, radially outwardly toward the 3D surface mesh model, such that the position of the intersection between the rays and the 3D surface mesh model are recorded, e.g., intersection points D1, D2. Step 10 may be repeated at each predefined interval to determine a series of intersection points along the surface topology of the 3D surface mesh model. At step 912, the overall length of a line extending across the surface of the 3D surface mesh model of the isolated anatomical feature, as defined by the intersection points determined at step 910, may be calculated based on the determined intersection points. FIG. 11 illustrates surface line SL extending across the surface topology of a 3D surface mesh model of an isolated anatomical feature.

For example, regarding cardiac image segmentation, once the automated segmentation has been completed, a 3D surface mesh model of the heart surrounding vessels will be created. This 3D data may then be automatically analyzed to assess specific lengths pertaining to the landmarks of the heart which may include, but are not limited to: atrium; ventricle; aorta; vena cava; mitral valve; pulmonary valve; aortic valve; tricuspid valve; myocardium; coronary arteries; left atrial appendages.

Figure 12:
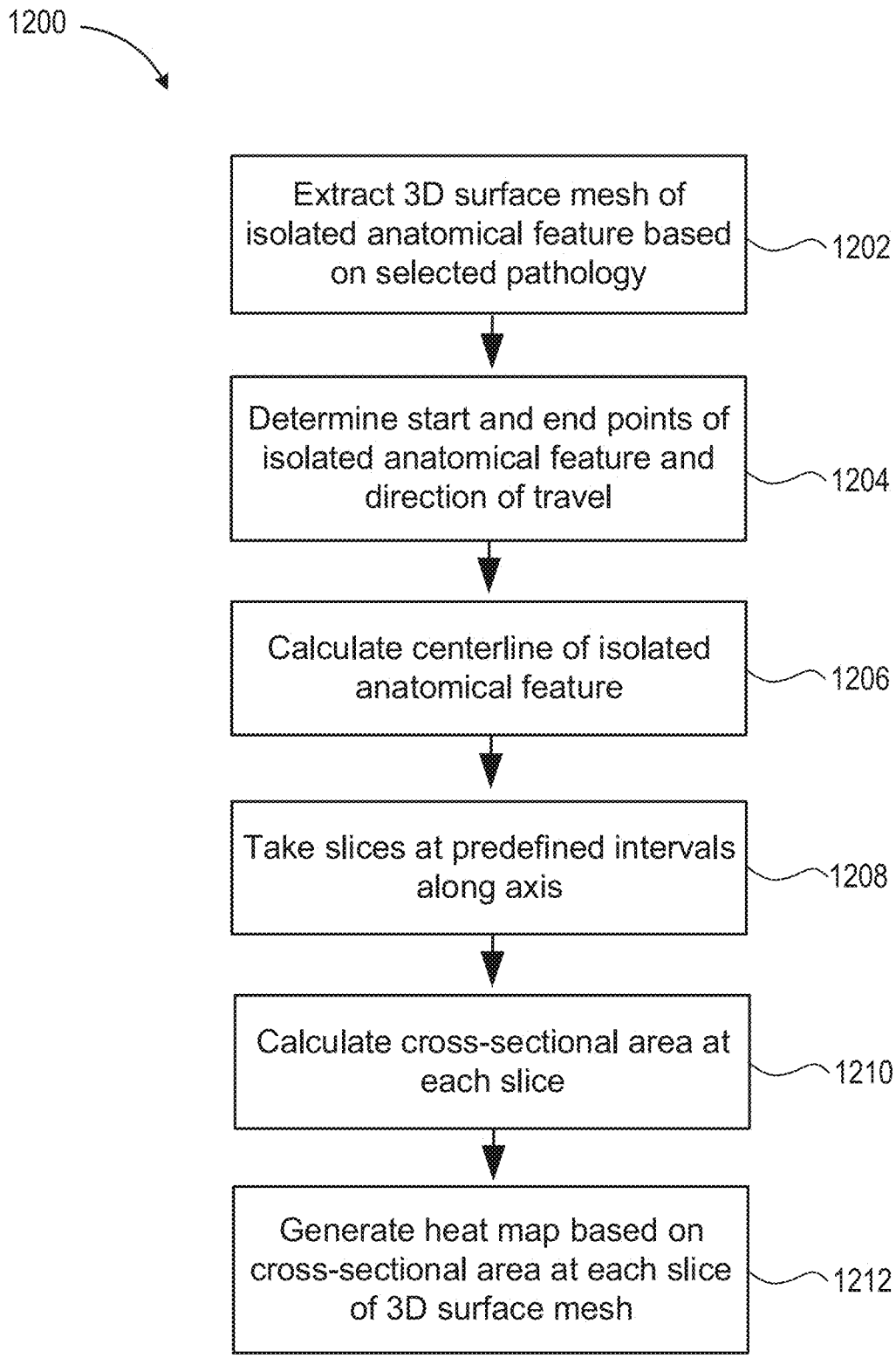
FIG. 12 is a flow chart illustrating exemplary method steps for generating a heat map of a patient specific anatomical feature based on volume in accordance with the principles of the present disclosure.

Referring now to FIG. 12, exemplary method 1200 for generating a heat map of a patient specific anatomical feature based on volume is provided. As described above, the cross-sectional area of the isolated anatomical feature at predefined intervals along an axis of the isolated anatomical feature may be determined, such that a heat map of the 3D surface mesh model may be generated based on cross-sectional areas of the 3D surface mesh model along the axis of the isolated anatomical feature. For example, at step 1202, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded. At step 1204, a start point and an end point of the isolated anatomical feature is determined, and an initial direction of travel may be determined consistent with the directional vector extending from the start point to the end point. At step 1206, the centerline of the isolated anatomical feature may be determined, e.g., via method 500 described above.

Figure 13A:
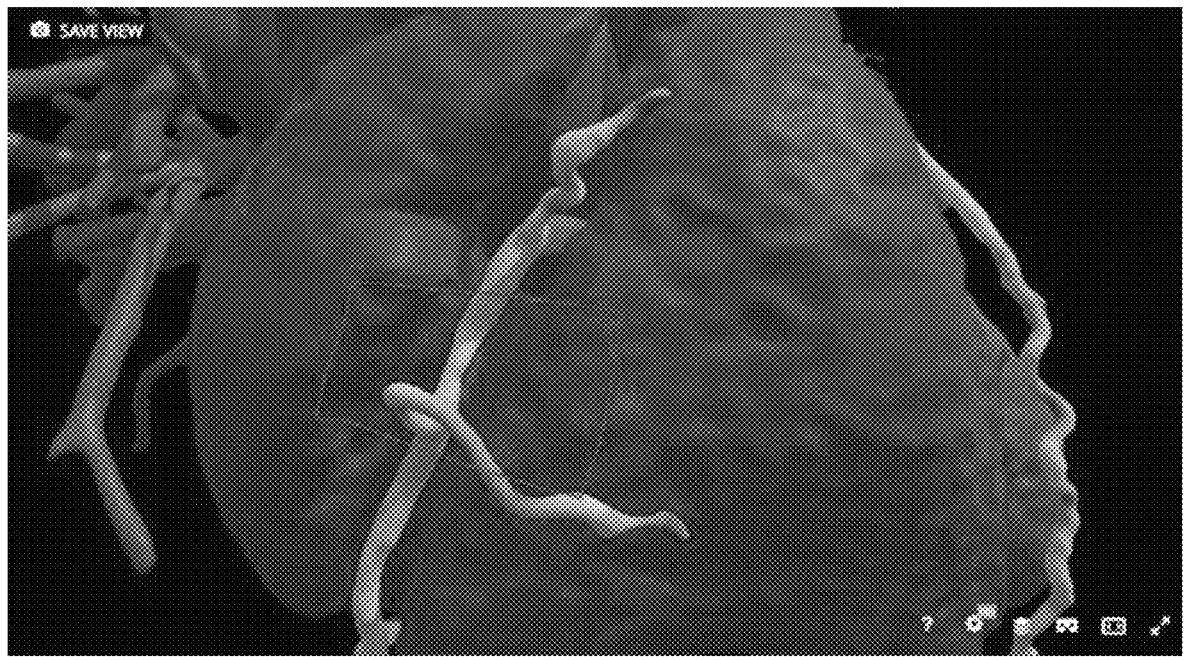
FIGS. 13A and 13B illustrate volume-based heat maps of a patient specific anatomical feature.
Figure 13B:
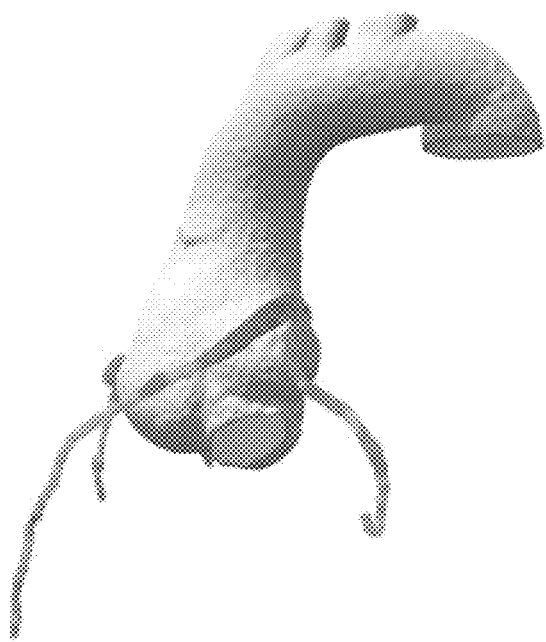

At step 1208, a predetermined step size may be determined, such that slices may be taken at regular intervals defined by the predetermined step size along the centerline of the isolated anatomical feature. Accordingly, a slice of the isolated anatomical feature may be taken at each interval perpendicular to the direction of travel along the centerline. At step 1210, using standard computational functions, the cross-sectional area at each slice of the isolated anatomical feature may be calculated, as defined by the perimeter of the isolated anatomical feature. At step 1210, a heat map may be generated based on the cross-sectional areas at each slice of the 3D surface mesh model, thereby visually indicating the change in volume throughout the isolated anatomical feature, as shown in FIGS. 13A and 13B.

Figure 14:
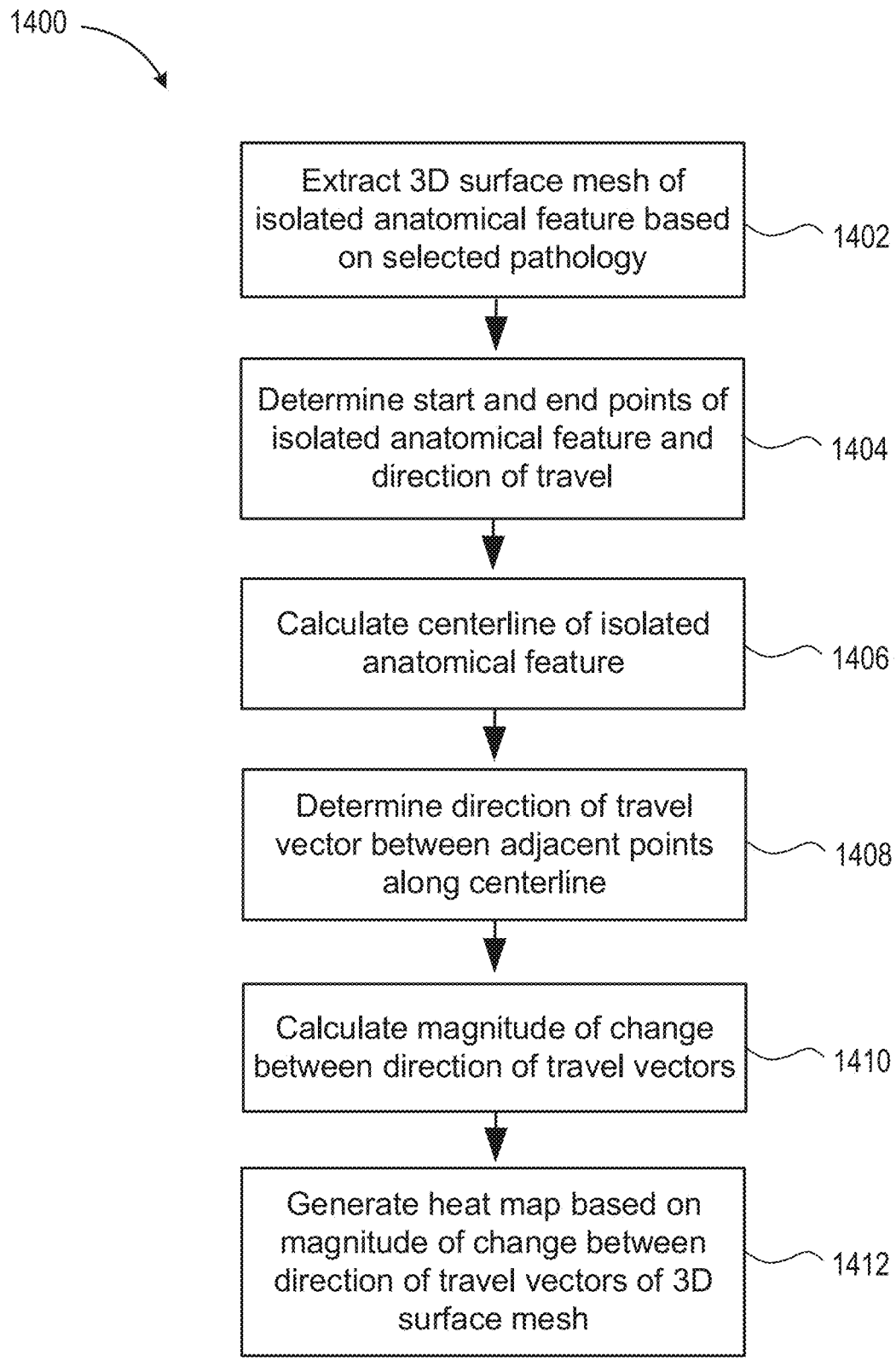
FIG. 14 is a flow chart illustrating exemplary method steps for generating a heat map of a patient specific anatomical feature based on tortuosity in accordance with the principles of the present disclosure.

Referring now to FIG. 14, exemplary method 1400 for generating a heat map of a patient specific anatomical feature based on tortuosity is provided. As described above, the direction of travel at predefined intervals of the centerline of the isolated anatomical feature may be determined, such that a heat map of the 3D surface mesh model may be generated based on the magnitude of change of the direction of travel along the axis of the isolated anatomical feature. For example, at step 1402, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded. At step 1404, a start point and an end point of the isolated anatomical feature is determined, and an initial direction of travel may be determined consistent with the directional vector extending from the start point to the end point. At step 1406, the centerline of the isolated anatomical feature may be determined, e.g., via method 500 described above.

Figure 15:
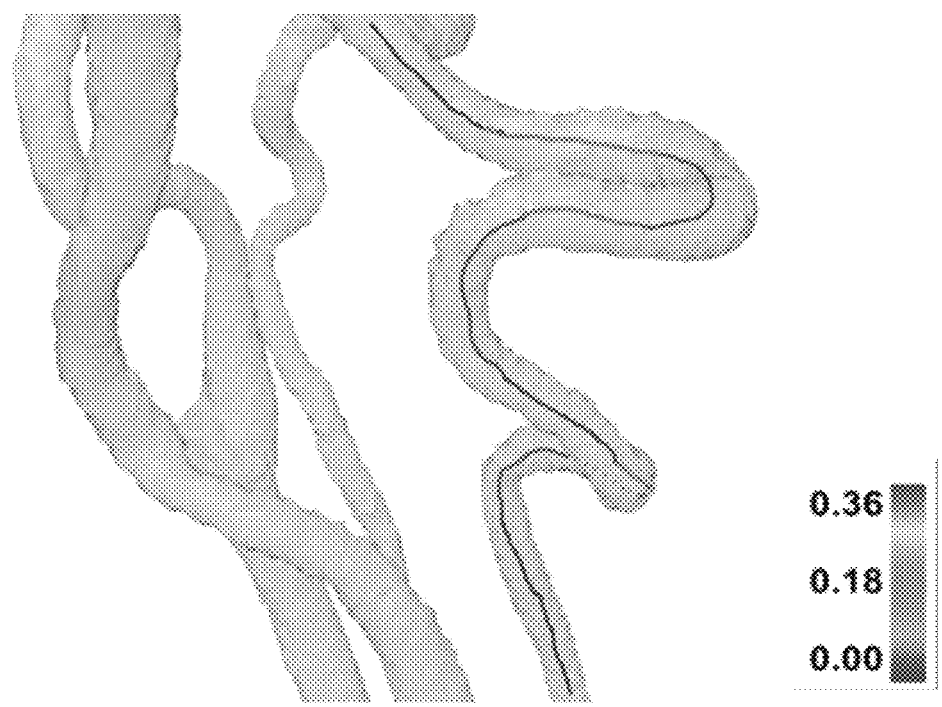
FIG. 15 illustrates a tortuosity-based heat map of a patient specific anatomical feature.

At step 1408, the direction of travel at predefined intervals of the centerline of the isolated anatomical feature may be determined, e.g., based on the directional vectors extending between adjacent center points along the centerline as described above. At step 1410, the magnitude of change between the direction of travel of adjacent intervals may be determined. For example, the magnitude of change may be calculated using the directional vectors associated with the respective directions of travel at each interval. At step 1412, a heat map may be generated based on the magnitudes of change between the direction of travel of adjacent intervals along the axis of the 3D surface mesh model, thereby visually indicating the tortuosity of the isolated anatomical feature, as shown in FIG. 15. Accordingly, the magnitude of change, e.g., angular changes, that are outputted from the analysis may be cross-referenced with an existing knowledge database of known classification angular deviations, and displayed to the user. The tortuosity value may be depicted as a total change in angle of the vessel and scored, e.g., 760 degrees rotation score.

Figure 16:
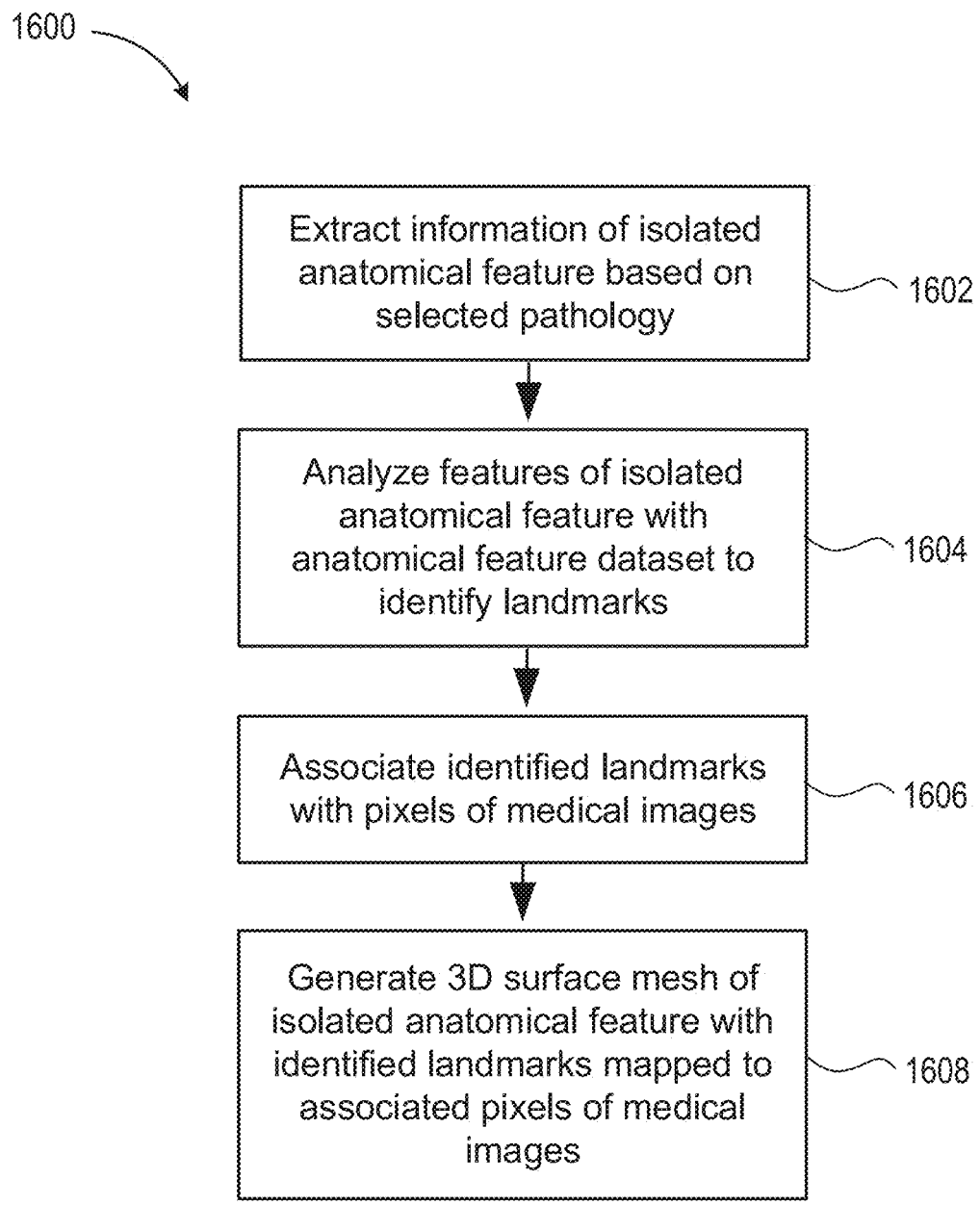
FIG. 16 is a flow chart illustrating exemplary method steps for generating a 3D surface mesh model of a patient specific anatomical feature with identified landmarks in accordance with the principles of the present disclosure.

Referring now to FIG. 16, exemplary method 1600 for generating a 3D surface mesh model of a patient specific anatomical feature with identified landmarks is provided. As described above with regard to FIG. 2, medical images, as shown in 1702 of FIG. 17A, may be automatically processed to identify patient specific anatomical features, as shown in 1704 of FIG. 17A, such that a 3D surface mesh model of the classified patient specific anatomical features within the medical images may be generated. Method 1600 further identifies corresponding landmarks of the patient specific anatomical features, e.g., a bone notch or heart valve, such that the landmarks may be depicted in the 3D surface mesh model. For example, prior to generation of the 3D surface mesh model based on the classified patient specific anatomical features, at step 1602, information indicative of a specific anatomical feature may be isolated from the data representing the patient specific anatomical features within the medical images based on the selected pathology, as shown in 1706 of FIG. 17A (anatomy delineation).

At step 1604, features of the isolated anatomical feature may be analyzed with an anatomical feature dataset to identify one or more landmarks of the isolated anatomical feature associated with the selected pathology. For example, the anatomical feature dataset may include knowledge of anatomical landmarks, e.g., existing semantically labeled anatomical feature datasets, associated with various patient specific anatomical features, such that the landmarks may be identified and individually labeled by establishing links between the classified, isolated anatomical feature and the anatomical feature dataset. At step 1606, the identified, labeled landmarks may be associated with pixels of the original medical images, as shown in 1708 of FIG. 17A. At step 1608, a 3D surface mesh model of the isolated anatomical feature may be generated depicting the identified landmarks mapped to the pixels of the medical images associated therewith, as shown in 1710 of FIG. 17A.

Figure 17A:
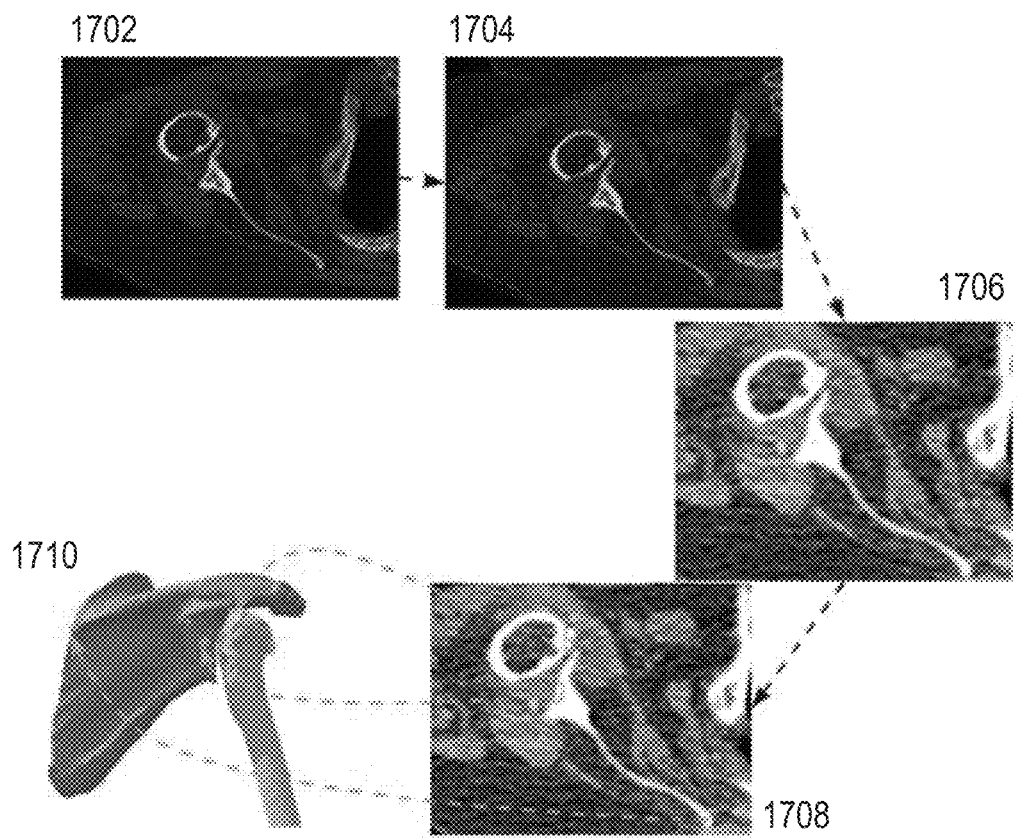
FIG. 17A illustrates exemplary method steps for mapping identified landmarks of a patient specific anatomical feature to a 3D surface mesh model in accordance with the principles of the present disclosure.
Figure 17B:
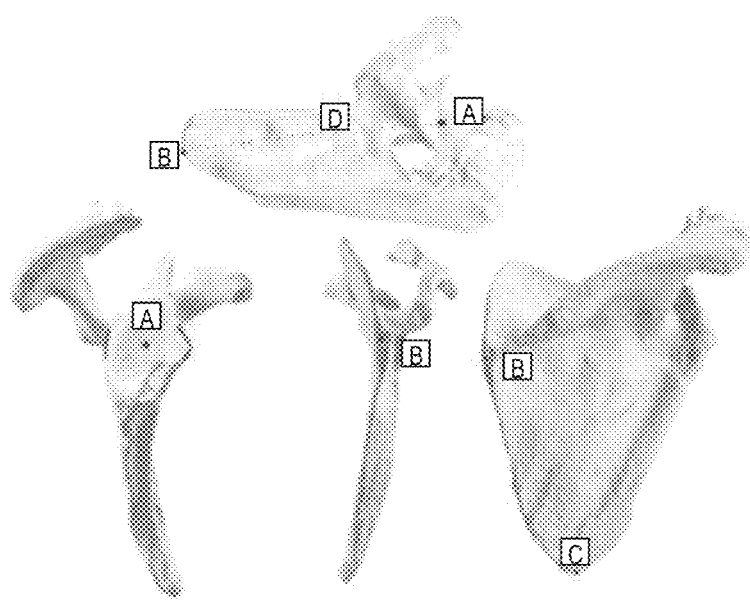
FIG. 17B illustrates identified landmarks of a patient specific anatomical feature mapped to a 3D surface mesh model.

The identified anatomical landmarks are a meaningful point in a patient's anatomy that has significance to its form or function, such as orientation and insertion points for other anatomical features. The identified landmarks may help surgeons ensure the landmarks correspond to a specific portion of anatomy and ensure its proper function and orientation. The identified landmarks further may be utilized within clinical practice as markers on anatomy to facilitate diagnosis and/or treatment of a patient, e.g., as an initial reference for anatomical guide fixation and trajectory planning. For example, specific anatomical landmarks identified for each bone may be automatically detected, such that a guide may be generated for cutting and drilling of the bone. Thus, the identified anatomical landmarks may be used as inputs for clinical functions have significant benefits. For example, FIG. 17B illustrates the following identified landmarks: (A) fossa center, (B) trigonum, (C), inferior angle, (D) center of spine of scapula, mapped to the isolated anatomical feature, e.g., a scapula for shoulder replacement. Accordingly, the identified landmarks may serve as a reference to provide guidance for cutting planes and drilling trajectories within bones, as well as for device fixation in the bone.

Figure 18:
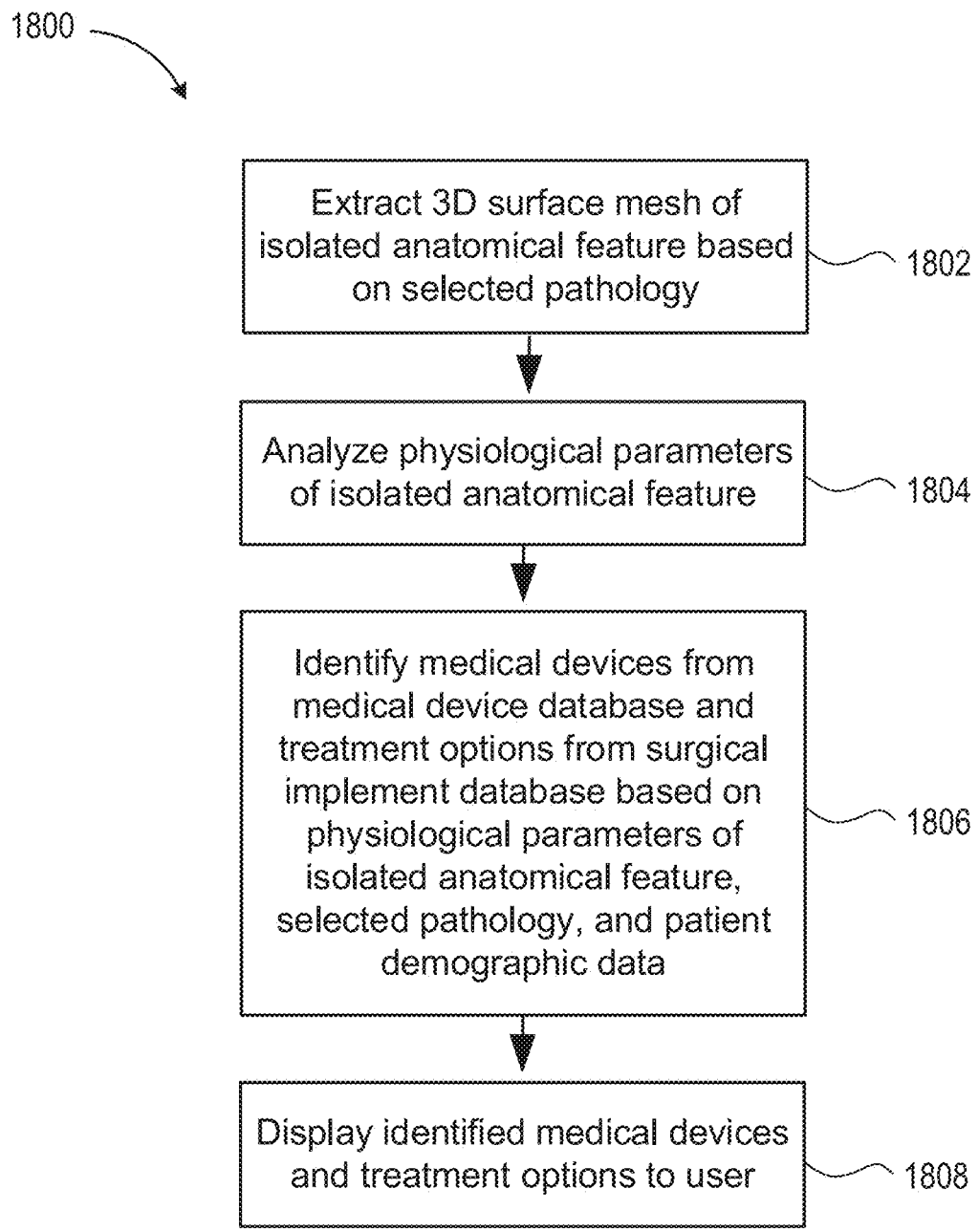
FIG. 18 is a flow chart illustrating exemplary method steps for identifying medical devices and treatment options for a pathology in accordance with the principles of the present disclosure.
Figure 19A:
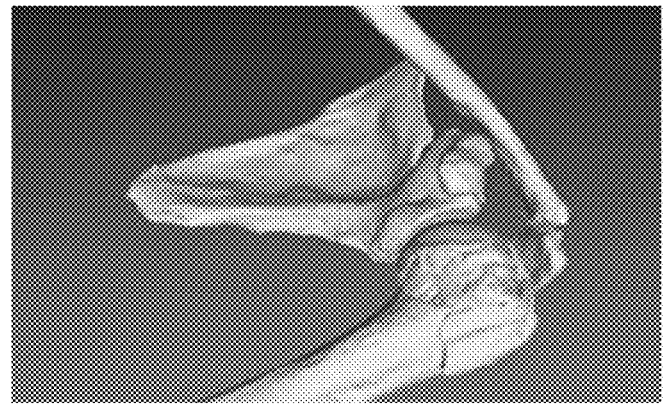
FIG. 19A illustrates a pathology of a bone.

Referring now to FIG. 18, exemplary method 1800 for identifying medical devices and treatment options for a pathology is provided. For example, at step 1802, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded, as shown in FIG. 19A. At step 1804, physiological parameters of the isolated anatomical feature may be analyzed, as described above, for example, to determine measurements such as volume, centerline, surface length, cross-sectional area, diameter, density, etc.

Figure 19B:
FIGS. 19B and 19C illustrate various medical devices that may be used for treatment of the pathology.
Figure 19C:

Based on the physiological parameters of the isolated anatomical feature as well as patient demographic data associated with the medical images, at step 1806, one or more medical devices and/or treatment options may be identified from a medical device database having knowledge of various medical devices including their function and specifications and/or a surgical implement database having knowledge of pathology-specific treatment options. For example, physiological parameters of the isolated anatomical feature may indicate the size of a selected pathology, such that a specific sized medical device that is known to be used to treat the selected pathology may be identified for use in treating the pathology. The identified medical devices may further be selected from an internal inventory, e.g., medical devices available or provided by a specific hospital. The knowledge datasets described herein may further include knowledge of the combination of anatomy with non-organic material, e.g., polymers, metals and ceramic, such that non-organic material may also be auto-segmented. In addition, the knowledge datasets may include knowledge of medical devices which may be used as inputs for creation of patient specific guides, e.g., knowledge of preexisting implants for the correction of bony pathologies. For example, known dimensions and variabilities of the devices may be used as inputs in the device's automated design. At step 1808, the identified medical devices and/or treatment options may be displayed to the user, such that the user may make an informed decisions regarding preoperative planning and treatment, as shown in FIGS. 19B and 19C.

The ability to provide the automated segmentation opens up a number of beneficial pathology specific applications. For example, some specific pathologies/treatments that require higher volume 3D models (virtual or physical) are listed in Table 1 below.

TABLE 1

| Where | Pathology | How to treat |
|---|---|---|
| C | LAA—left atrial appendage | Occlusion device (watchman) |
| C | Mitral valve regurgitation | Mitral valve replacement |
| C | Aortic valve regurgitation | TAVI/TAVR—Transcatheter aortic valve implantation |
| C | Aortic aneurysms | Patient specific stent |
| IR | AAA—Abdominal aortic aneurysms | Patient specific Stent |
| C | Septal defects (ventricle or atrium) | Occlusion device |
| C | Coronary heart disease | Arthrectomy/Angioplasty via catheter or coronary bypass |
| N | Ischemic Stroke | Aspiration stent or no stent retrieval catheter |
| N | Hemorrhagic stroke | Craniotomy |
| N | Neuro Aneurysm (ICA) | Stent, coil or clip |
| O | Bone Fractures | Plates or Patient specific instrumentation |

TABLE 1-continued

| Where | Pathology | How to treat |
|---|---|---|
| O | Primary orthopaedic replacement failure (Hip, knee, pelvis) | Revision instrument—Patient specific guide & Patient specific instrumentation |
| O-On | Osteosarcoma | Patient specific guide & Patient specific instrumentation |
| O | Scoliosis | Plates or Patient specific instrumentation |
| O | Osteoarthritis—hip | Joint replacement, primary hip replacement Ortho instruments |
| O | Osteoarthritis—knee | Joint replacement, primary knee replacement Ortho instruments |
| O | Osteoarthritis—knee | Joint replacement, primary shoulder replacement Ortho instruments |
| ON | General oncology (lung, liver, Kidney, skull base, brain) | Resection or radiation of tumor mass |
| M | Midface deformities | Le Fort procedure—facial reconstruction with osteotomies |
| G | Colon disease—Bowel cancer, Crohn's disease,, colitis, diverticulitis | Stoma and colostomy bag |
| G | Prostate enlargement, bladder cancer & urinary incontinence | Urinary catheter |
| O | Cruciate ligament/meniscus tears | Knee replacements |
| C | Aortic Stenosis | Transcatheter aortic valve replacement |

Figure 20:
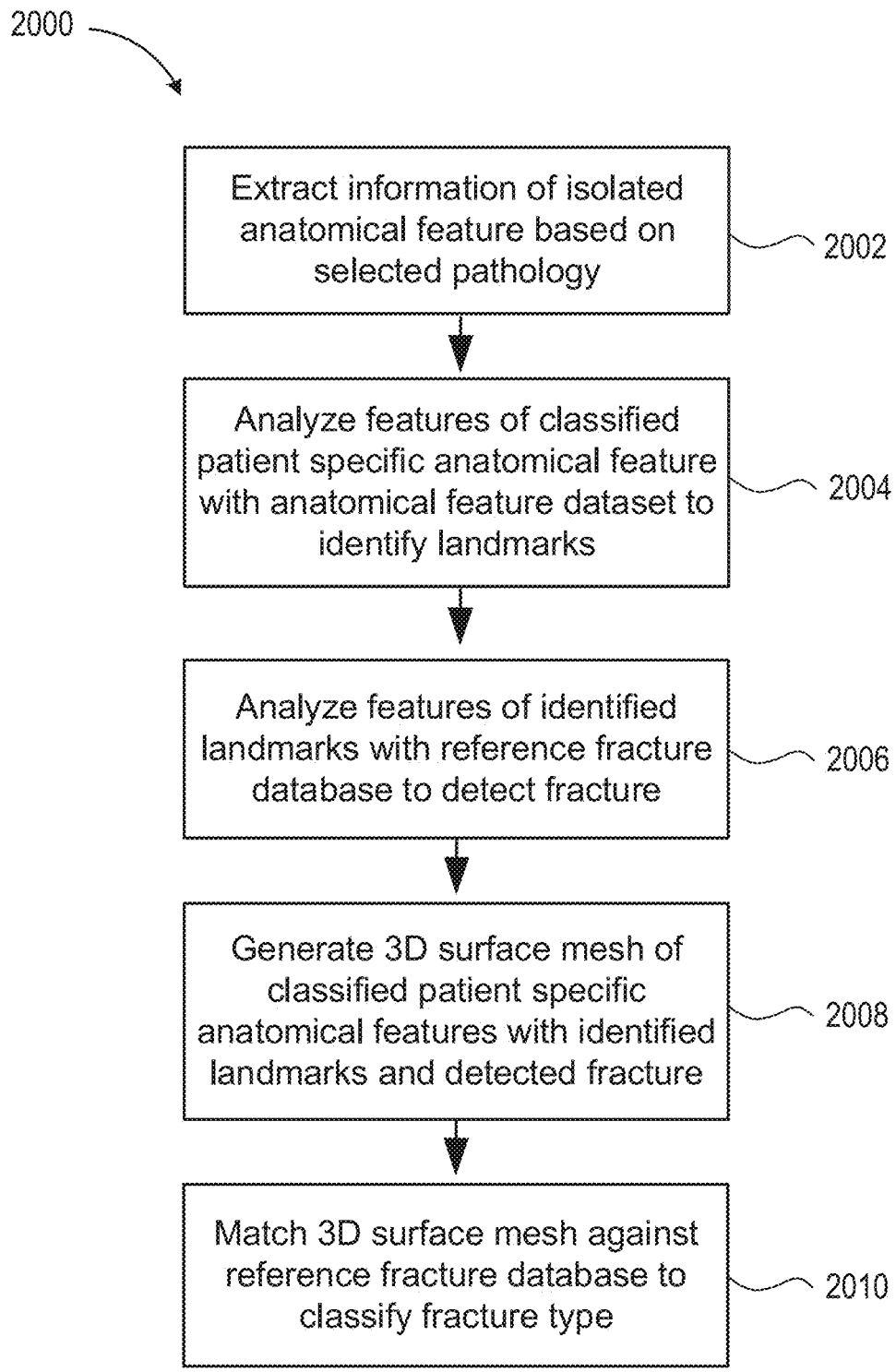
FIG. 20 is a flow chart illustrating exemplary method steps for detecting and classifying a fracture of a patient specific anatomical feature in accordance with the principles of the present disclosure.
Figure 21A:
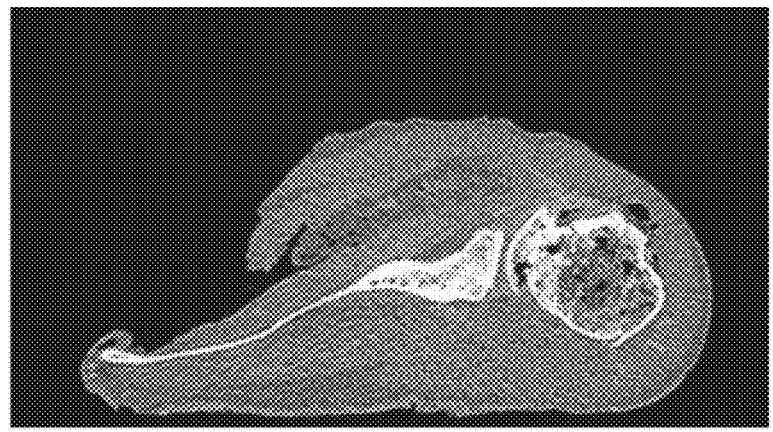
FIGS. 21A to 21D illustrate mapping a detected fracture of a patient specific anatomical feature to a 3D surface mesh model in accordance with the principles of the present disclosure.
Figure 21B:
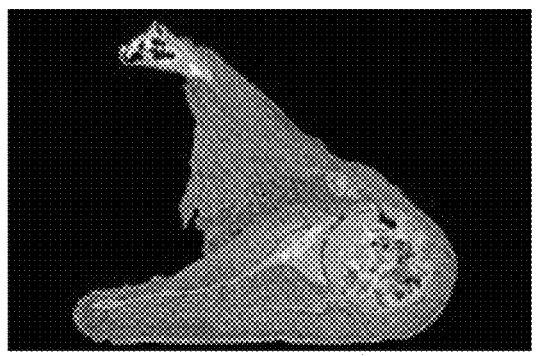
Figure 21C:

O—Ortho
C—cardiac/cardiology
N—Neuro
G—General
M—Max fax
On—Oncology
IR—Interventional radiology Referring now to FIG. 20, exemplary method 2000 for detecting and classifying a fracture of a patient specific anatomical feature is provided. As described above with regard to FIG. 2, medical images, as shown in FIG. 21A, may be automatically processed to identify patient specific anatomical features, such that a 3D surface mesh model of the classified patient specific anatomical features within the medical images may be generated. Method 1600 further detects/identifies corresponding fractures of the patient specific anatomical features, e.g., in a bone such as the tibia, fibia, or medial malleolus, such that the fractures may be depicted in the 3D surface mesh model. For example, prior to generation of the 3D surface mesh model based on the classified patient specific anatomical features, at step 2002, information indicative of a specific anatomical feature may be isolated from the data representing the patient specific anatomical features within the medical images based on the selected pathology, as shown in FIGS. 21B and 21C.

At step 2004, features of the isolated anatomical feature may be analyzed with an anatomical feature dataset to identify one or more landmarks of the isolated anatomical feature, e.g., a bone notch, associated with the selected pathology. As described above, the anatomical feature dataset may include knowledge of anatomical landmarks associated with various patient specific anatomical features, such that the landmarks may be identified and individually labeled by establishing links between the classified, isolated anatomical feature and the anatomical feature dataset. At step 2006, features of the identified landmark may be analyzed with an reference fracture database to identify one or more fractures of the identified landmark of the isolated anatomical feature associated with the selected pathology.

Figure 21D:
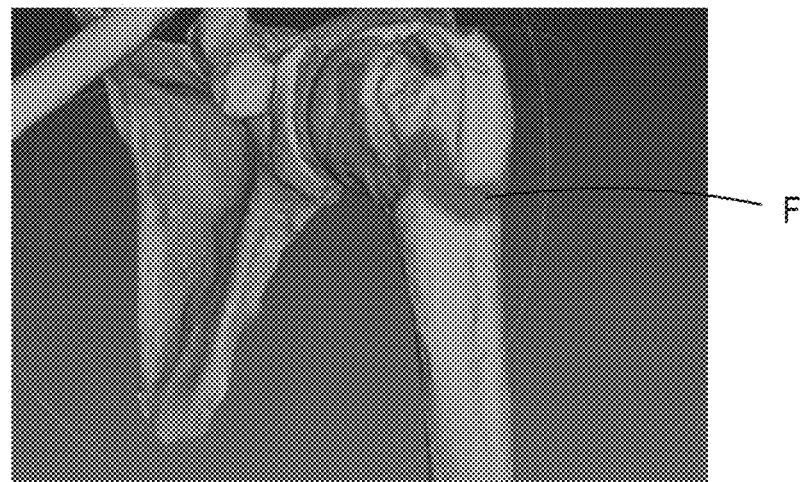

The reference fracture database may include knowledge of various fractures, e.g., existing semantically labeled reference fracture datasets, associated with various patient specific anatomical features, such that the fractures may be identified and individually labeled by establishing links between the classified, isolated anatomical feature and the anatomical feature dataset. At step 2008, a 3D surface mesh model of the isolated anatomical feature may be generated depicting the identified landmarks and detected fracture F, as shown in FIG. 21D. Moreover, at step 2010, the 3D surface mesh model may be matched against the reference fracture database to classify the fracture type.

Figure 22:
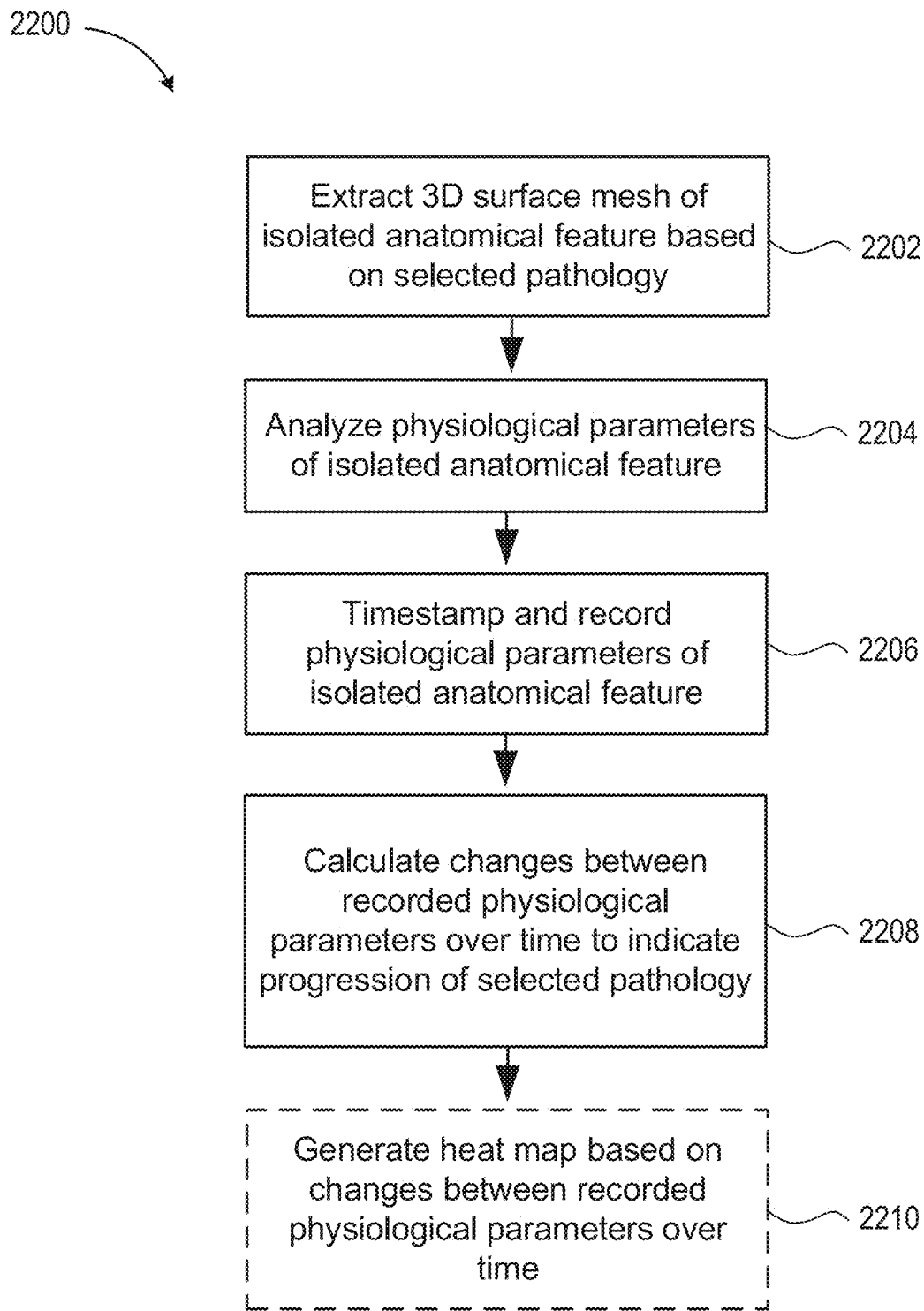
FIG. 22 is a flow chart illustrating exemplary method steps for tracking progression of a pathology over time in accordance with the principles of the present disclosure.
Figure 23A:
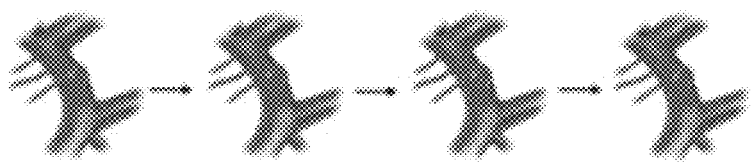
FIGS. 23A to 23F illustrate various progressions of pathologies over time.
Figure 23B:
Figure 23C:
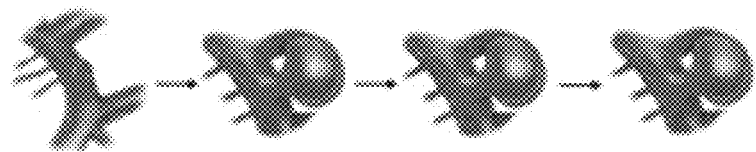
Figure 23D:
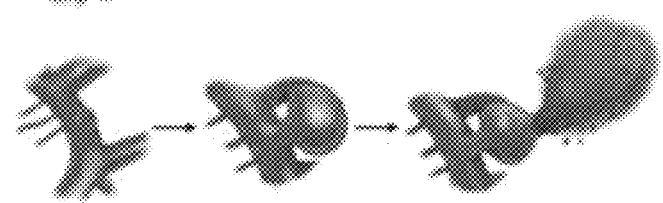
Figure 23E:
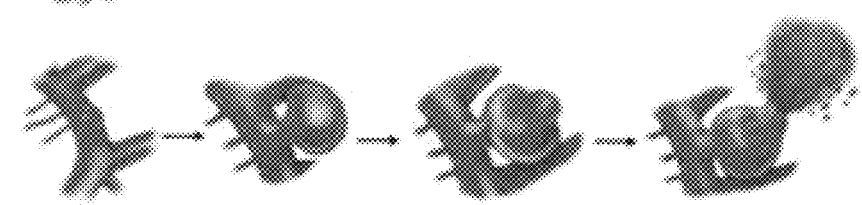
Figure 23F:
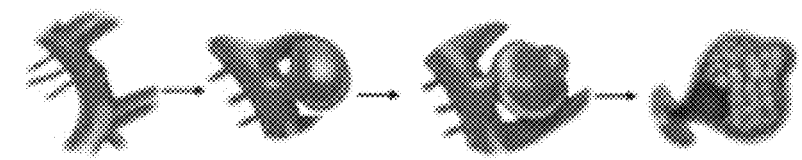
Figures 24A, 24B, 24C, 24D, 24E, 24F:
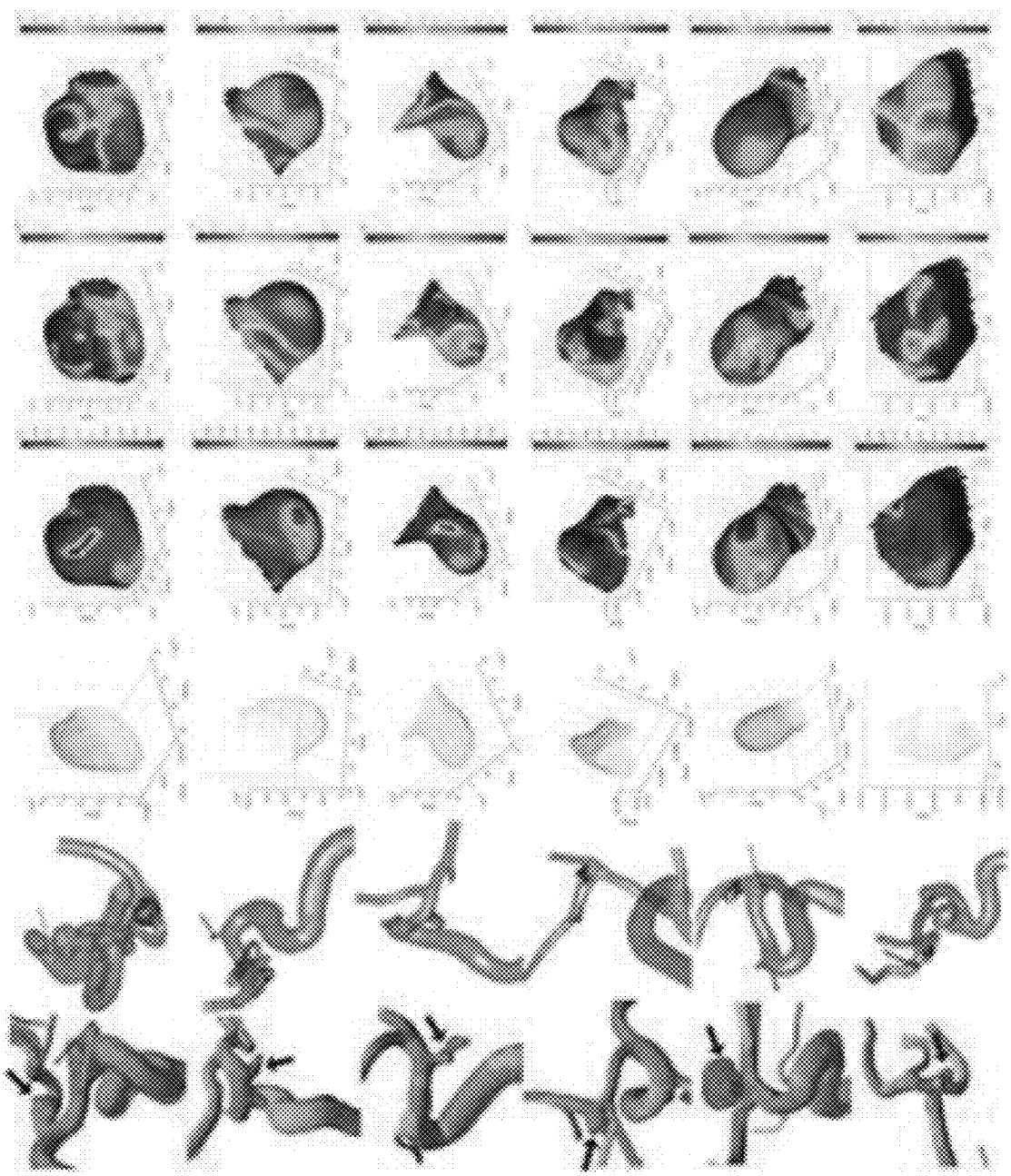
FIGS. 24A to 24F illustrate heat maps of various progressions of pathologies over time.

Referring now to FIG. 22, exemplary method 2200 for tracking progression of a pathology over time is provided. For example, at step 2202, a specific anatomical feature may be isolated from the patient specific anatomical features within the medical images based on the selected pathology, as described above, such that a 3D surface mesh model of the isolated anatomical feature may be extracted from the 3D surface mesh model of the patient specific anatomical features and recorded. At step 2204, physiological parameters of the isolated anatomical feature may be analyzed, as described above, for example, to determine measurements such as volume, centerline, surface length, cross-sectional area, diameter, density, etc.

For example, once the automated segmentation has been completed, a 3D surface mesh model of the aneurysm and vascular anatomy may be generated. This 3D data may then be automatically analyzed to assess specific lengths pertaining to the aneurysm morphology, which may include, but are not limited to measurements of the aneurysm neck, diameter measurements of the aneurysm at maximum distances, and measurements of center points of the superior and inferior aneurysm necks.

At step 2206, the analyzed physiological parameters of the isolated anatomical feature may be timestamped and recorded, such that over time, there is a chronological record of the physiological parameters for a specific patient. At step 2208, changes between the recorded/timestamped physiological parameters over time may be calculated to indicate, e.g., progression and prognosis of the selected pathology. For example, FIGS. 23A to 23F illustratively show growth of various aneurysms over time, leading to eventual rupture. Optionally, at step 2210, a heat map may be generated to visually depict the changes between the recorded/timestamped physiological parameters over time, as shown in FIGS. 24A to 24F.

Figure 25:
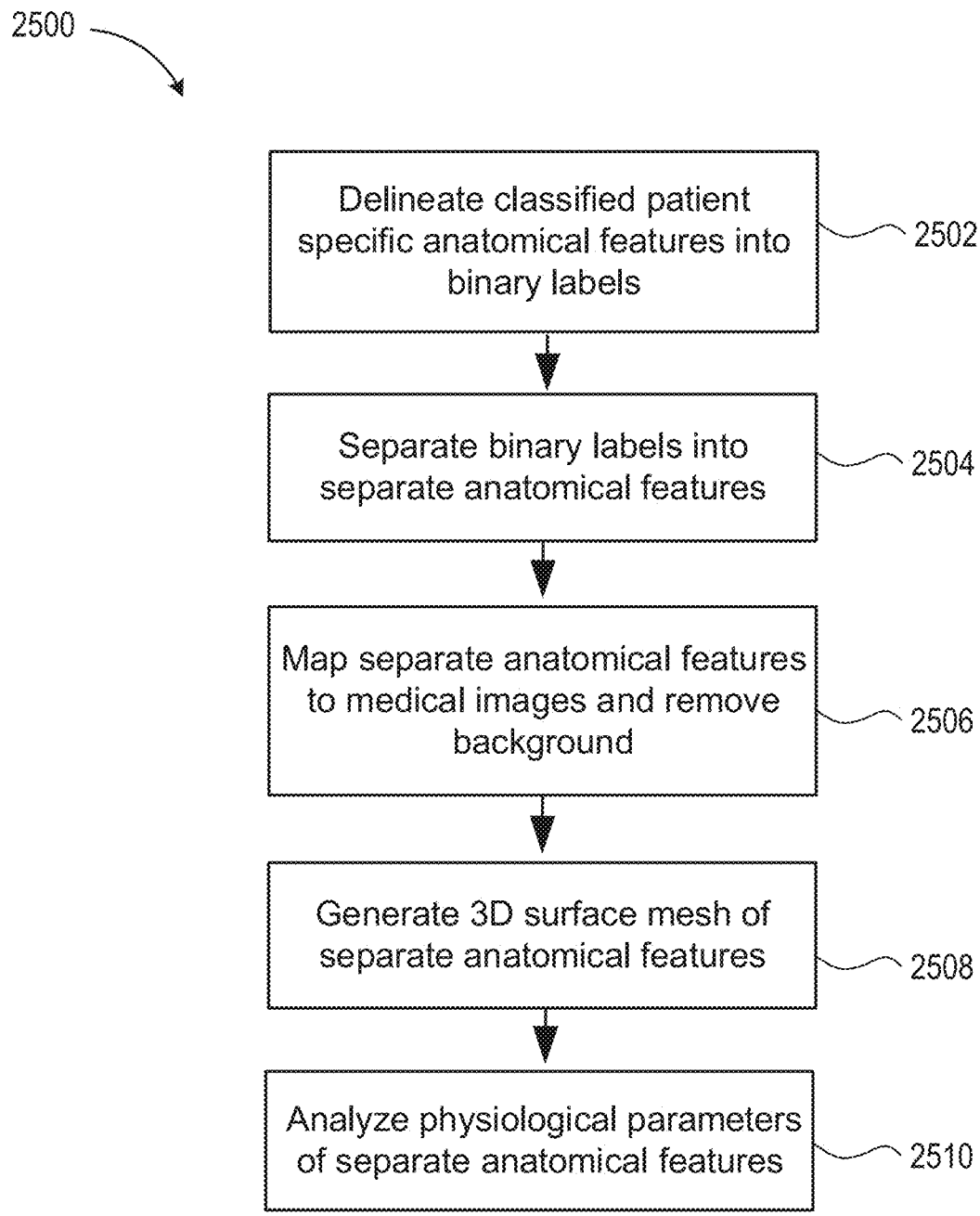
FIG. 25 is a flow chart illustrating exemplary method steps for analyzing physiological parameters of separate anatomical features in accordance with the principles of the present disclosure.
Figure 26:
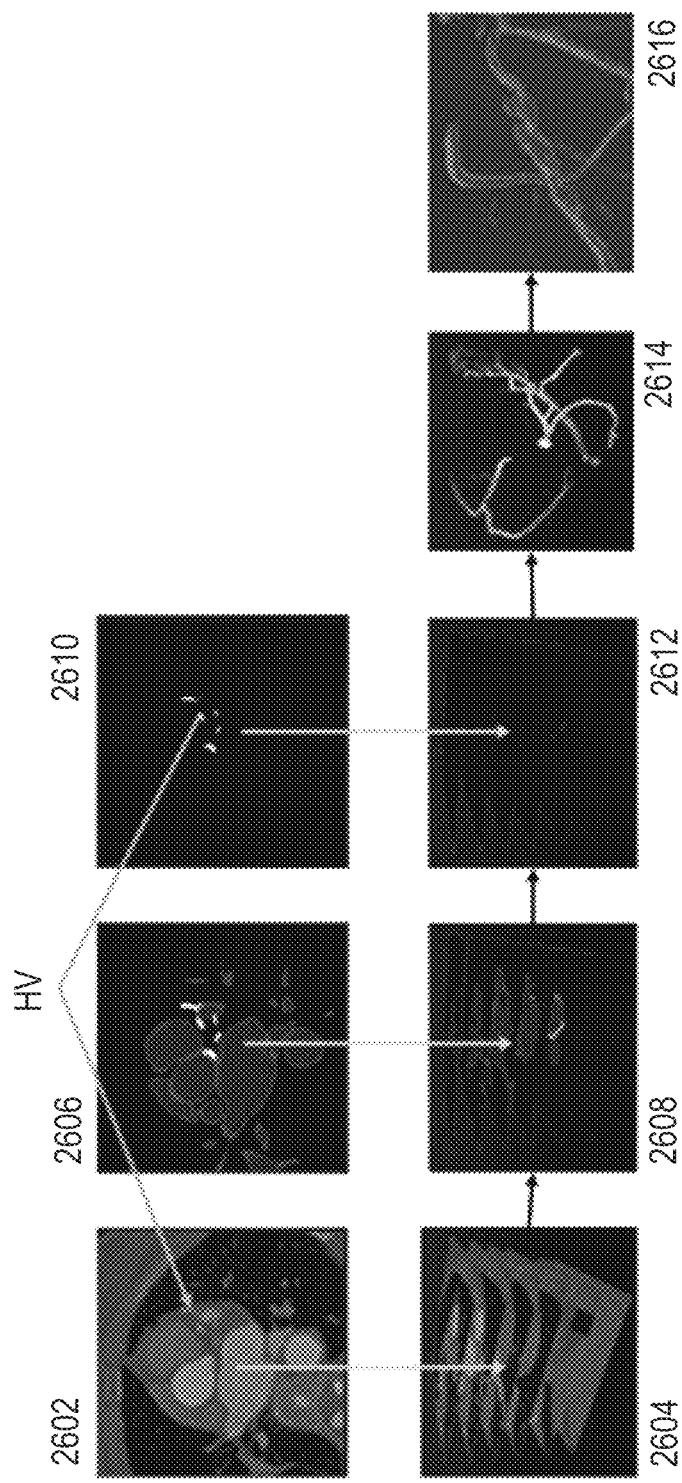
FIG. 26 illustrates generation of 3D volumetric rendering of separate anatomical features in accordance with the principles of the present disclosure.

Referring now to FIG. 25, exemplary method 2500 for semantic volume rendering is provided. A single medical image 2602 of a stack of medical images 2604 is shown in FIG. 26. Volume rendering is an important solution that is adopted by medical professionals globally to visualize medical imaging datasets in 3D space. They work by mapping pixel characteristics such as specific color, intensity, or opacity to specific voxels within the 3D scene. There are deficiencies associated with this method of imaging whereby overlapping and deep structures are not easily visualized in detail. Thus, to cure these deficiencies, method 2500 generates 3D surface mesh models of separate anatomical features, such that physiological parameters of the separate anatomical features may be analyzed.

For example, the results of the automatic image segmentation may take the form of a series of binary pixel arrays contained in medical images, e.g., DICOM files. When assembled into a volume, the binary pixel arrays may be used to mask the areas of the source pixel volume that are not relevant to the identified anatomy. The remaining Hounsfield value volume may then be rendered using standard volume rendering techniques with the color transfer function, such that pixel intensity may be determined based on the Hounsfield values. Moreover, the length of the anatomical feature, e.g., a vessel, may be calculated based on the output from the automated segmentation algorithm and subsequent 3D reconstruction. The data extracted from the 3D reconstruction may then be automatically analyzed to output a length from one specific anatomical landmark or abnormality to another, e.g., the length from the aortic arch to the thrombus in the case of a stroke. The measurement in the case of a vessel may be calculated by creating a center point on a cross section of the vessel, and extrapolated the center points through the vessel and joining the center points to create a centerline of the anatomy. This centerline may then be automatically measured and outputted to the user as a length value.

Figure 27B:
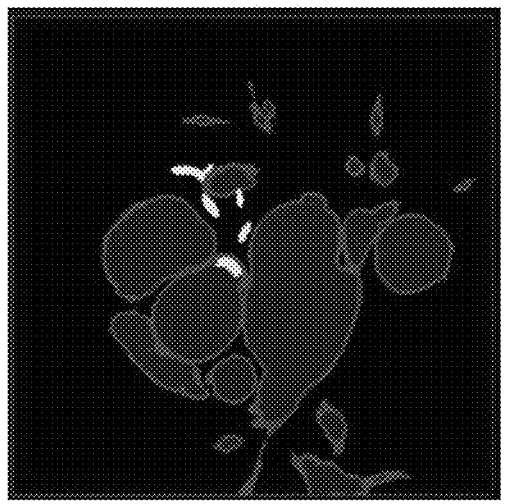
FIG. 27B illustrates separate anatomical features overlaid on the original medical image.

For example, at step 2502, the classified patient specific anatomical features generated using the segmentation algorithm described above are delineated into binary labels, e.g., bone/not bone, vessel/not vessel, organ/not organ, etc. At step 2504, the binary labels are separated into separate anatomical features, e.g., myocardium of heart, aorta, coronary arteries, etc. At step 2506, the separate anatomical features are mapped to the original medical images, such that only the original grey scale values or Hounsfield units for the separate anatomical features are shown in the medical images, as shown in 2606 and 2608 of FIG. 26 and FIG. 27B, and the background may be removed from the medical images as shown in 2610 and 2612 of FIG. 26 and FIG. 27C, leaving visible only the separate anatomical features depicted in the original grey scale values or Hounsfield units.

At step 2508, a 3D surface mesh model of the separate anatomical features may be generated. The 3D surface mesh model may define a surface of the separate anatomical features, as shown in 2614 of FIG. 26. Additionally or alternatively, the specific colors of transparency values may be mapped to labeled 3D surface mesh model to generate a volumetric render, as shown in 2616 of FIG. 26 and FIG. 27D. For example, a color map of the pixel intensities may be mapped directly to the 3D voxel intensities within only the segmentation to allow for specific volumetric visualization of the isolated anatomical feature. The voxels may be given a specific color automatically depending on the intensities of the original image, which may be indicative of normal blood flow or lack thereof. The ability to color specific regions of interest such as a clot, break, or anatomy, allows for greater insight into a specific pathology of a region.

Figure 27D:
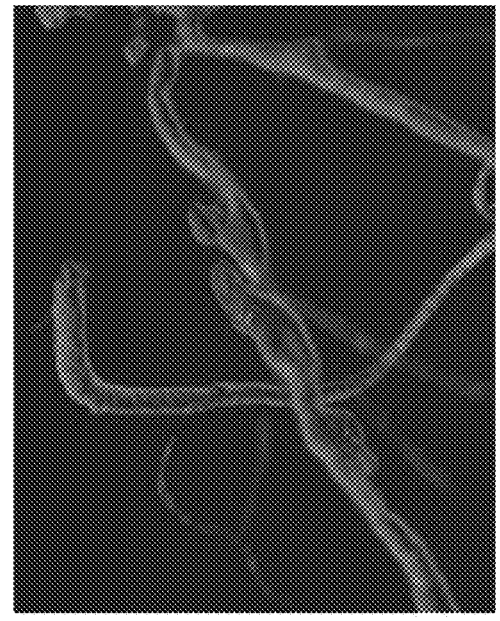
FIG. 27D illustrates a 3D volumetric rendering of the separate anatomical features.
Figure 27A:
FIG. 27A illustrates an original medical image of a patient specific anatomical feature.
Figure 27C:
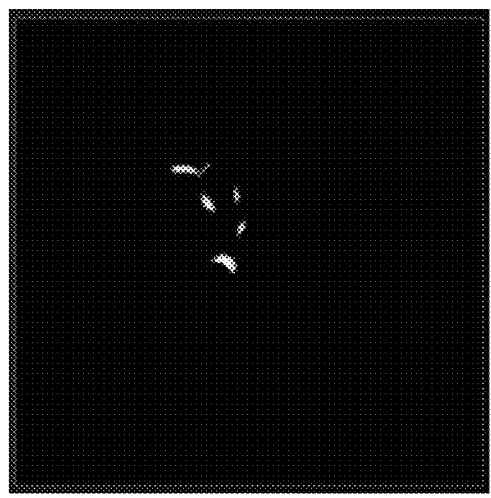
FIG. 27C illustrates the separate anatomical features with the background removed.
Figure 28A:
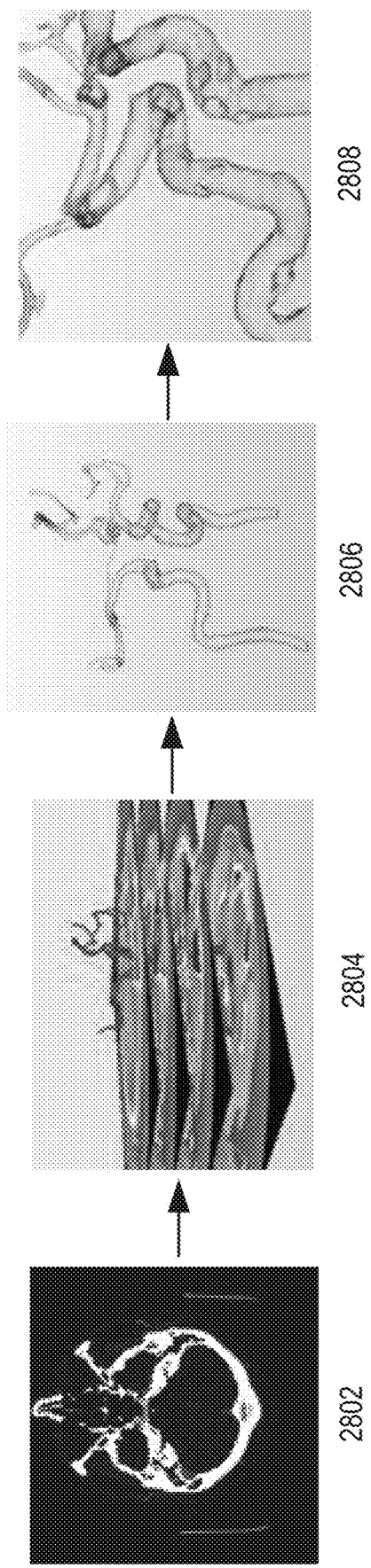
FIGS. 28A and 28B illustrate exemplary method steps for measuring an occlusion of a patient specific anatomical feature in accordance with the principles of the present disclosure.
Figure 28B:
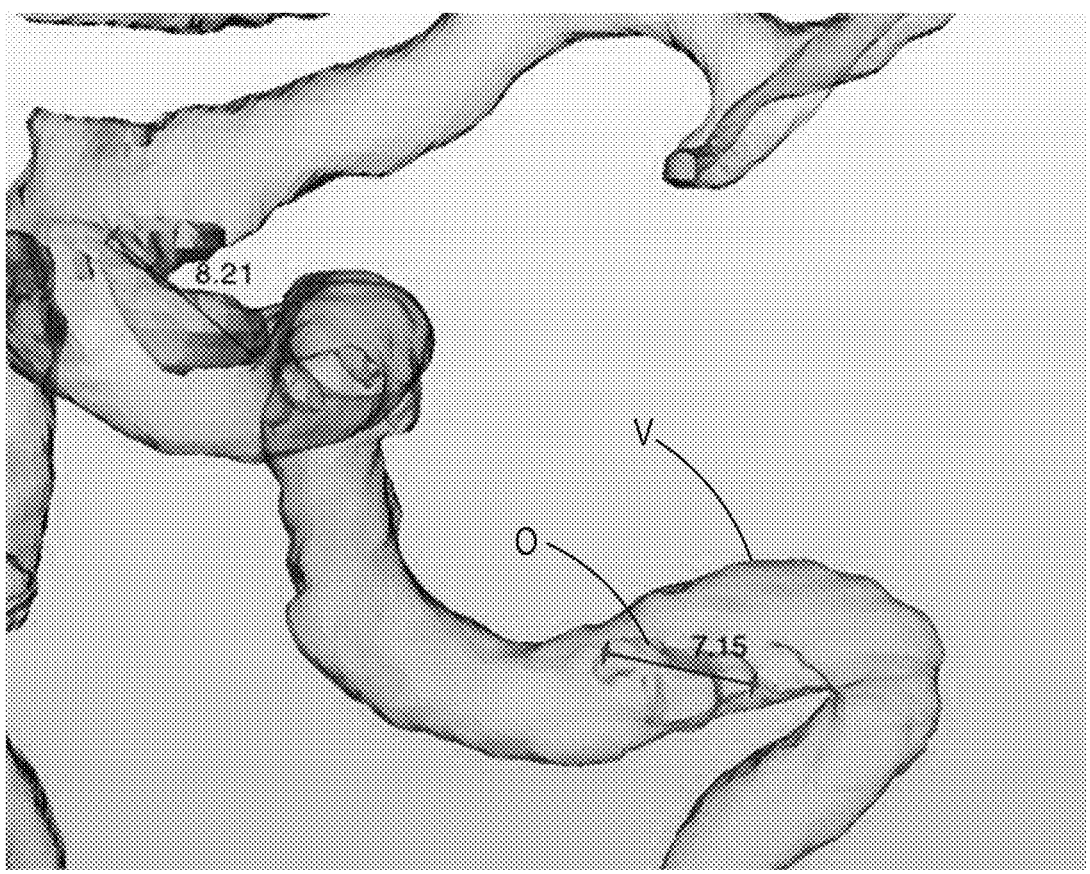

As shown in FIG. 27D, the 3D volumetric render may indicate the presence of a clot/occlusion. This data may then be rendered on an end-user application such that the 3D volumetric render may be rotated or otherwise manipulated and viewed. This data also may be used to indicate to the user if calcification is present from, e.g., a grouping of high intensity pixels, and further may provide a calcification "score" by indicating the percent of the clot or occlusion that is representative of the calcified structure. For example, predictions of the occlusions/calcifications may be made and applied as a mask on the original medical image, such that the background portions of the medical image may be removed, as shown in 2802 of FIG. 28A. Accordingly, a 3D surface mesh model may be generated that takes into account the pixel intensity of the various materials, as shown in 2804, 2806, and 2808 of FIG. 28A. As shown in FIG. 28B, the size of occlusion O depicted in vessel V of the 3D volumetric render may be measured, e.g., for assisting in the diagnosis and treatment for stroke patients.

The 3D volumetric render may be set by the user or automatically derived to visualize specific features by referencing the anatomical features depicted in the volumetric render, such as clots within vascular structures, coronary arteries, neuro vessels, thereby indicating a potential stroke. Accordingly, the medical images may be automatically segmented and reconstructed, e.g., by utilizing CTA's/XA/NM vessel imaging for the patient, to create a 3D representation of both a vessel and associated occlusions using machine learning from a semantically labeled 3D anatomical knowledge dataset that may be easily viewed on a mobile device or similar platform.

Once the 3D surface mesh model is generated from the automated segmentation, it will be possible to generate a number of measurements about the anatomy or pathology in the medical scan. Moreover, the scaling information along with reference points permits placement of the patient specific anatomical features within a physical scene. At the most simple level, physical measurements may be generated of the mesh, or any sub-mesh, or otherwise delineated region in the physical scene, which may include: length, breadth, height, angles, curvature, tortuosity of a mesh, etc. Given a filled structure, measurements may also be made of the volume, surface area, and diameter.

Derived properties of the materials to be segmented may also be measured. At a basic level, these may include thickness of the material (blood vessel or bone), and a known derivation from the normal (patient or general), which may permit generation of predictions about, e.g., the likely pressure required to break the material, or simply supply a visualization of the thickness and stress lines. Visualization of any of the above mentioned measurements provides great value as any more information available to the surgeon would be helpful in the determination of the best course of action for treatment, and would provide the ability to give an accurate analysis of the diagnosis. This may be achieved through a simple overlay of the derived variable over the mesh or by providing the data for additional analysis of the input/desired attribute.

Aside from the determining the structure of a patient specific anatomical feature as described above, an extracted polygonal model may further provide a convenient basis for determining numerous useful measurements that would otherwise be difficult to ascertain from volumetric pixel data alone, e.g., bone and vessel dimensions, angle and tortuosity differentials and relative scales, density etc. Normally determining these measurements would require careful manual assessment of a mesh in order to identify areas of interest and meaningful reference points. However, the exploratory geometric algorithms described herein provides a reliable automated alternative. For example, the following pseudocode outlines how vessel length, diameter and curvature information may be automatically collected without human intervention:

```
getVesselInfo (mesh) {
  -get Bounding Box of input mesh
    -get minimum and maximum coordinates along each axis
    -any vertices existing at these extreme points can be presumed to form
  part of the circular opening of a vessel
    -build circular/elliptical entry points by clustering previously identified
    extreme vertices
    -get centre points of vessel openings
    -determine inward direction of vessels from volume
    -for each entry point centre
      -while ray cast hasn't collided with planes defined by vessel entry
      points
        -create new measurement line
        -raycast at different equidistant angles
        -take longest distance
        -advance along distance line
        -centre in vessel diameter by calculating centre of smallest
        diameter line
        -(save diameter value for determining thickness differential later)
        -add new location to measurement line
        -in the event of multiple peaks in the array of distances
          -foreach branch continue march
      -remove exit point from entrypoint list
  -return resulting directional paths
```

Figure 29:
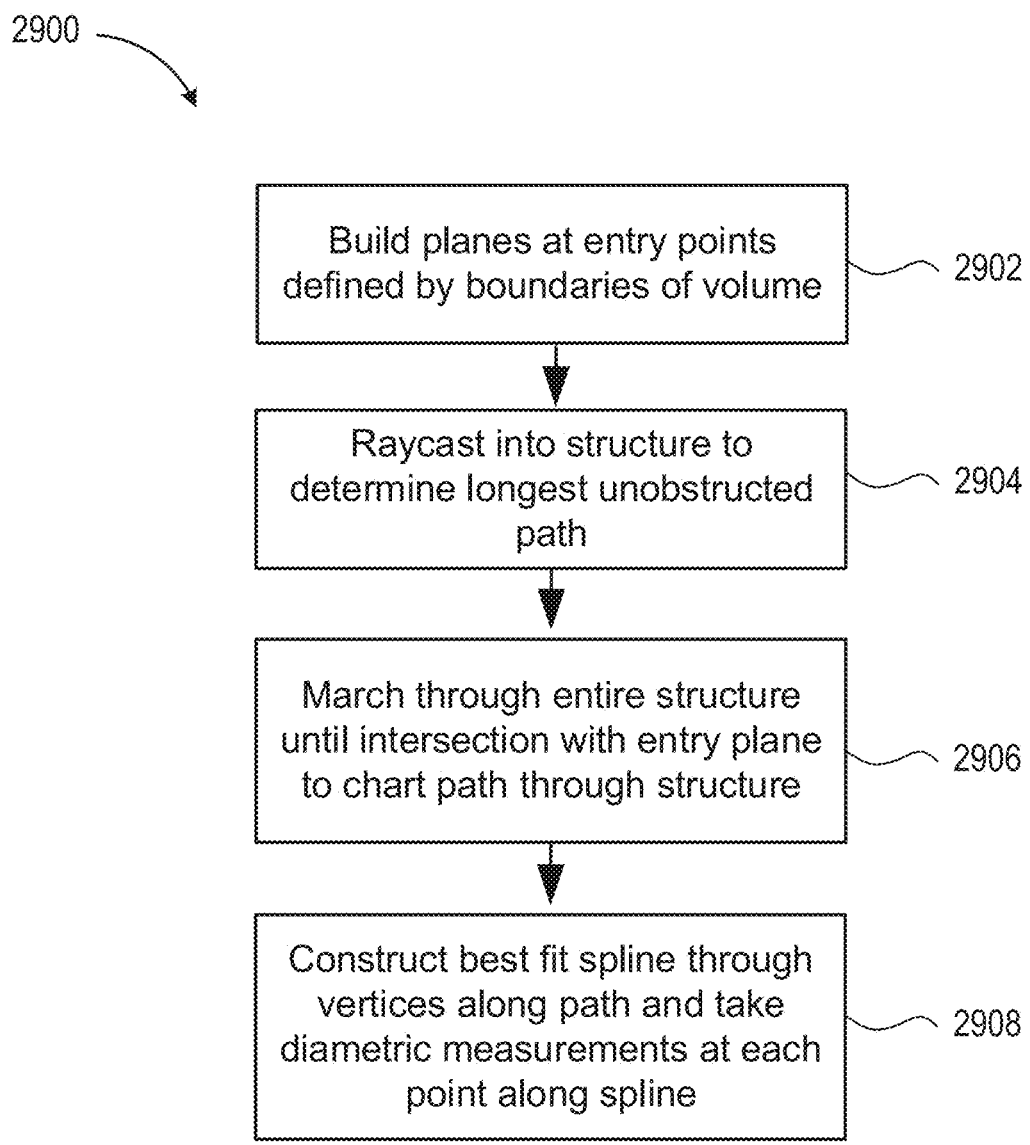
FIG. 29 is a flow chart illustrating exemplary method steps for analyzing physiological parameters of separate anatomical features in accordance with the principles of the present disclosure.

Referring now to FIG. 29, exemplary method 2900 for analyzing physiological parameters of separate anatomical features is provided. Some of the steps of method 2900 may be further elaborated by referring to FIGS. 30A to 30E, which depict a 2D example of a cross-section of a vessel with branching paths. FIG. 30A illustrates branched vessel V. At step 2902, planes P1, P2, P3 may be built at the entry points of vessel V, defined by the boundaries of the volume of vessel V, as shown in FIG. 30B. At step 2904, center points C1, C2, C3 of entry planes P1, P2, P3, respectively, may be calculated, as shown in FIG. 30C. As shown in FIG. 30C, multiples ray may be raycast from center point C3 into the structure of vessel V to determine the longest unobstructed path within vessel V. Because of the branching paths of vessel V, there are two peak points PP1, PP2 depicted in FIG. 30C. This may be determined by assessing the number of inflection points in the graph of distance values. Having determined that there are numerous paths forward at this point in the algorithm, each branch may be assessed individually by branching off the control flow.

At step 2906, the entire structure of vessel V is marched through until the rays cast at each point along lines L1, L2 intersect with entry planes P2 and P3, respectively, as shown in FIG. 30D, resulting in a series of vertices charting each of the paths through vessel V. At step 2908, a best fit spline line may be constructed through the vertices along lines L1, L2, as shown in FIG. 30E, such that diametric measurements may be taken at each point along lines L1, L2 to thereby provide a complete representation of vessel V, of which slope/tortuosity, diameter, internal volume, etc. may be determined.

Moreover, working from the pseudocode described above, the presence of a pathology such as an aneurysm would result in the search point getting stuck in a loop. Whenever the points of the measurement line begin to repeatedly change direction. The algorithm may break out of the search loop and presume that an aneurysm has been entered. Accordingly, the physiological measurements of the aneurysm may be determined, e.g., by determining points around the entry to the aneurysm, building entry plane to the aneurysm, determining the center point of the entry plane, and raycasting into the aneurysm structure to determine the most distant point, and when the max distance has been determined, building a line between the entry plane and max distant point, and begin checking perpendicular distances by raycasting.

The results of the segmentation may be quantified by, e.g., measuring the density of a segmented area, identifying the proximity to other pieces of anatomy, and identifying and delineating boundaries, especially with regard to oncology. Once a region has been identified and delineated within the physical scene, statements about the region may be made in relation to other structures within the scene. For example, delineating tumor boundaries and understanding their distance from key structures in the anatomical neighborhood would be useful to oncologists. Moreover, the density of a given structure would provide clinically relevant information, e.g., in the case of oncology, it would provide insight into hypoxia within the tumor, and in the case of a blood clot, it would allow insight into how the clot could be treated.

The ability to measure the density and thickness of an anatomical region would allow the ability to provide guidance on, e.g., screw selection in trauma applications or catheter diameter in vascular applications. Moreover, the ability to measure the diameters along an anatomical feature would allow the diameter measurements to be cross-referenced with a medical device database to indicate to the surgeon the best sized device for that patient.

The machine learning based algorithms described herein may be trained and predicted on the axial axis, which is typically the axis that the medical scans are carried out in. A modification to the machine learning based algorithm may involve changing the prediction function, and another modification may involve changing the training and the prediction function. For example, a modification to the machine learning based algorithm may include making predictions in all three axis and then merging the results. This approach would work best where the voxels are isotropic, as in the case with the rimasys data. The merging of the predictions may follow a number of different strategies, for example, taking an average (mean) of the three results for a given pixel/voxel, or more complex solutions such as taking a weighted average of an axial slice plus the others. Alternatively, it would be possible to switch to a different primary axis, e.g., switching from an axial axis to a sagittal.

Training the algorithm on all three axes may take advantage of the additional information from the different axes. Thus, an axial inference model, a sagittal inference model, and a coronal model may be trained. As described above, the results of all three predictions may be combined with a simple merging strategy. However, preferably, either the output layer of the three models may be combined in a larger network or an ensemble model may be created that combines their results.

As described in U.S. Patent Appl. Pub. No. 2021/0335041, the algorithm may to work natively in 3D, which may be very expensive from a memory allocation point of view. One other approach to mitigate this restriction would be to consider a cube rather than a slice at a time. The advantage of this approach is that it may be possible to take into consideration the more pertinent and immediate context in the training, such that instead of considering a large thick slab, the algorithm is trained on small cubes of volume, which are slid over the entire volume.

The sandwich approach described in U.S. Patent Appl. Pub. No. 2021/0335041 may be extended to incorporate a larger number of slices, may also more explicitly incorporate the pixels from the surrounding slices in the model. For example, instead of using additional channels in the image, multiple channels, e.g., three channels, of most image formats may be leveraged to achieve this compression. By making the surrounding images into full images, the number of surrounding images in a scan may be generically increased. As the size of GPUs increase, the number of surrounding images in a scan may also be increased. Moreover, The algorithm may implement a version of D-Unet which takes into account the 3D contextual information (via 3D convolution kernels), and the amount of slices the model analyzes at a time may be increased to provide the algorithm much more spatial context. This architecture upgrade together with improvements to the loss functions and access to more data has resulted in increasingly better segmentation models.

Figure 31:
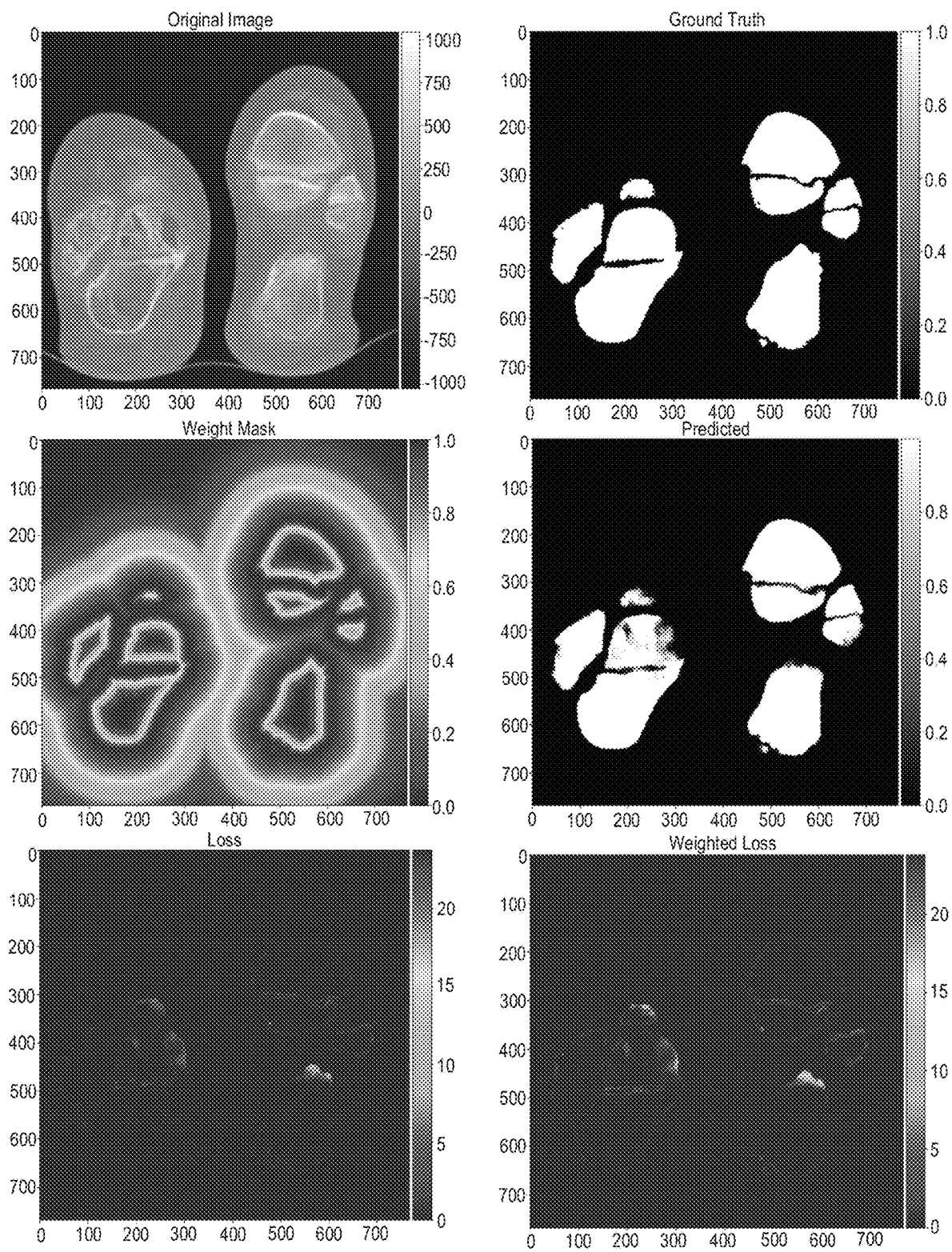
FIG. 31 illustrates weight masks generated with the Euclidean distance weight approach, as well as their effect on the loss function in accordance with the principles of the present disclosure.

Moreover, the methods described herein further may utilize an Euclidean distance weight approach to influence the loss component in the machine learning model training process. This approach helps guide the learning process to focus on areas of greater importance. For example, in orthopedics segmentation, the most difficult errors to detect/find and fix are small connections between bones that are very close to each other; whereas, small holes on the inside of the bones are more simple to correct. FIG. 31 illustrates weight masks generated with the Euclidean distance weight approach, as well as their effect on the loss function, e.g., categorical cross entropy.

A multi-schema approach to ground truth dataset for training is provided. Specifically, there are many different segmentation labeling schemas that may be used to adapt the training labels depending on the goal of the model to be trained. For example, as it may be very difficult to define the inner materials of trauma bones, they are generally segmented as hollow, and thus the predictions from a trauma model trained on hollow bone labels are much easier to work with, as shown in Table 2 below.

TABLE 2

Bone Segmentation Labelling Schemas

| Original Labels | Meaning | Outer Bone | Hollow Bone | Solid Bone | Solid Bone Only |
|---|---|---|---|---|---|
| 0 | Background | 0 (background) | 0 (background) | 0 (background) | 0 (background) |
| 1 | External | 0 (background) | 0 (background) | 0 (background) | 0 (background) |
| 2 | Outer trabecular | 1 (bone) | 1 (bone) | 1 (bone) | 1 (bone) |
| 3 | Inner trabecular | 0 (background) | 0 (background) | 1 (bone) | 1 (bone) |
| 4 | Outer cortical | 1 (bone) | 1 (bone) | 1 (bone) | 1 (bone) |
| 5 | Inner cortical | 0 (background) | 1 (bone) | 1 (bone) | 1 (bone) |
| 6 | Outer marrow | 1 (bone) | 1 (bone) | 1 (bone) | 1 (bone) |
| 7 | Inner marrow | 0 (background) | 0 (background) | 1 (bone) | 1 (bone) |
| 8 | Artifact | 2 (artifact) | 2 (artifact) | 2 (artifact) | 0 (background) |
| 9 | Air | 0 (background) | 0 (background) | 0 (background) | 0 (background) |

Figure 32:
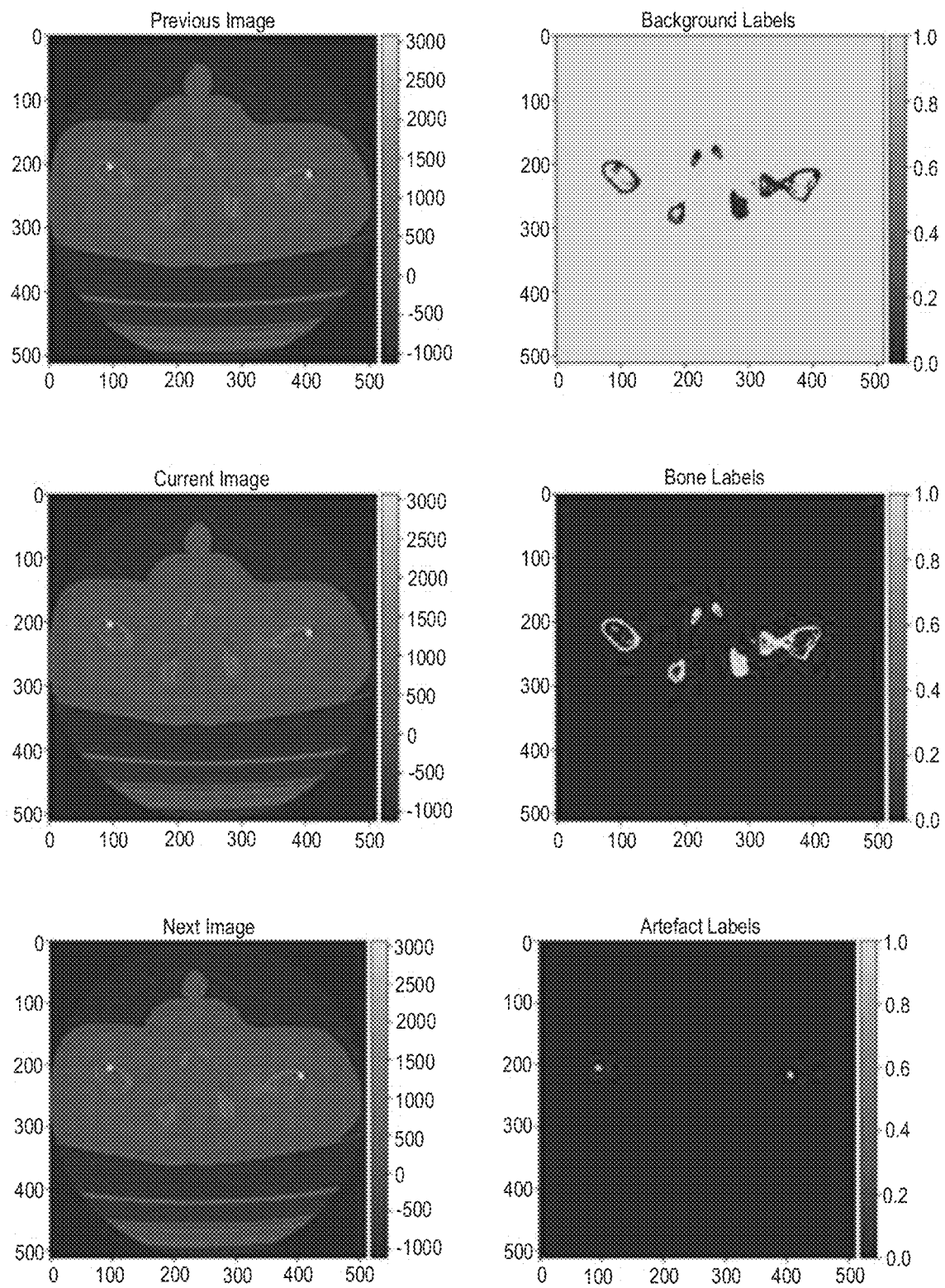
FIG. 32 illustrates various segmentations of bone within medical images for training purposes in accordance with the principles of the present disclosure.

FIG. 32 illustrates various segmentations of bone within medical images using the multi-schema approach to ground truth data for training purposes, as described above. Similarly, Table 3 illustrates cardiac segmentation labelling schemas used with the multi-schema approach to ground truth data.

TABLE 3

Cardiac Segmentation Labelling Schemas

| Original Labels | Meaning | Cardiac | Cardiac Only |
| --- | --- | --- | --- |
| 0 | Background | 0 (background) | 0 (background) |
| 1 | External | 0 (background) | 0 (background) |
| 2 | Blood-flow | 1 (blood-flow) | 1 (blood-flow) |
| 3 | Myocardium | 2 (myocardium) | 2 (myocardium) |
| 4 | Artifact | 3 (artifact) | 0 (background) |
| 5 | Calcification | 4 (calcification) | 1 (blood-flow) |

Figure 33:
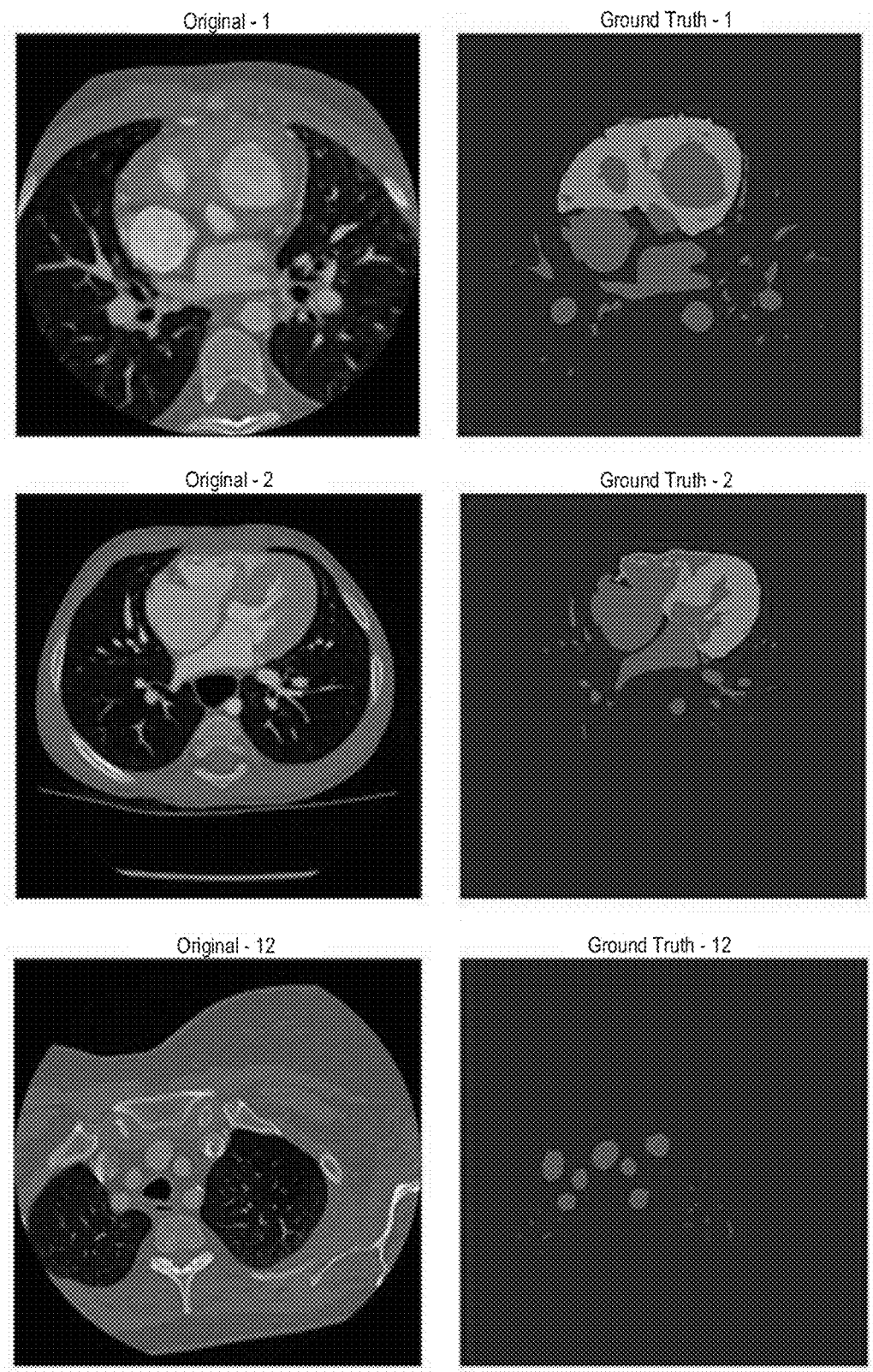
FIG. 33 illustrates various segmentations of a myocardium within medical images of ground truth data for training purposes in accordance with the principles of the present disclosure.

FIG. 33 illustrates various segmentations of a myocardium within medical images of ground truth data for training purposes.

These same techniques for adapting label schemas may be used to define normal versus pathological tissues, or lack of tissue in some examples, which will allow semantic segmentation of a pathology as a region of interest, and further allow pathology specific workflows to be automatically started. Moreover, the multi-schema approach of the using multiple labels to differentiate anatomies and pathologies may be used to semantically label each anatomical feature of the human body. Examples of various schema labels may include, but are not limited to: Nasal; Lacrimal; Inferior Nasal Concha; Maxiallary; Zygomatic; Temporal; Palatine; Parietal; Malleus; Incus; Stapes; Frontal; Ethmoid; Vomer; Sphenoid; Mandible; Occipital; Rib 1; Rib 2; Rib 3; Rib 4; Rib 5; Rib 6; Rib 7; Rib 8 (False); Rib 9 (False); Rib 10 (False); Rib 11 (Floating); Rib 12 (Floating); Hyoid; Sternum; Cervical Vertebrae 1 (atlas); C2 (axis); C3; C4; C5; C6; C7; Thoracic Vertebrae 1; T2; T3; T4; T5; T6; T7; T8; T9; T10; T11; T12; Lumbar Vertebrae 1; L2; L3; L4; L5; Sacrum; Coccyx; Scapula; Clavicle; Humerus; Radius; Ulna; Scaphoid; Lunate; Triquetrum; Pisiform; Hamate; Capitate; Trapezoid; Trapezium; Metacarpal 1; Proximal Phalange 1; Distal Phalange 1; Metacarpal 2; Proximal Phalange 2; Middle Phalange 2; Distal Phalange 2; Metacarpal 3; Proximal Phalange 3; Middle Phalange 3; Distal Phalange 3; Metacarpal 4; Proximal Phalange 4; Middle Phalange 4; Distal Phalange 4; Metacarpal 5; Proximal Phalange 5; Middle Phalange 5; Distal Phalange 5; Hip (Ilium, Ischium, Pubis); Femur; Patella; Tibia; Fibula; Talus; Calcaneus; Navicular; Medial Cuneiform; Middle Cuneiform; Lateral Cuneiform; Cuboid; Metatarsal 1; Proximal Phalange 1; Distal Phalange 1; Metatarsal 2; Proximal Phalange 2; Middle Phalange 2; Distal Phalange 2; Metatarsal 3; Proximal Phalange 3; Middle Phalange 3; Distal Phalange 3; Metatarsal 4; Proximal Phalange 4; Middle Phalange 4; Distal Phalange 4; Metatarsal 5; Proximal Phalange 5; Middle Phalange 5; Distal Phalange 5; Circle of Willis; Anterior Cerebral Artery; Middle Cerebral Artery; Posterior Cerebral Artery; Lenticulostriate Arteries; brachiocephalic artery; right common carotid; right subclavian artery; vertebral artery; basilar artery; Posterior cerebral artery; posterior cerebral artery; posterior communicating artery; left common carotid artery; internal carotid artery (ICA); external carotid artery (ECA); left subclavian artery; right subclavian artery; internal thoracic artery; thyrocervical trunk; costocervical trunk; left subclavian artery; aorta; Vena Cava; axilla; axillary artery; brachial artery; radial artery; ulnar artery; descending aorta; thoracic aorta; abdominal aorta; hypogastric artery; external iliac artery; femoral artery; popliteal artery; anterior tibial artery; arteria dorsalis pedis; posterior tibial artery; tricuspid valve; pulmonary valve; mitral valve; aortic valve; Right Ventricle; Left ventricle; Right atrium; Left atrium; Liver; Kidney; Spleen; Bowel; Prostate; Cerebrum; Brainstem; Cerebellum; Pons; Medulla; Spinal cord; Frontal lobe; Parietal lobe; Occipital lobe; Temporal lobe; Right coronary artery; left main coronary; left anterior descending; left circumflex artery.

Hybrid data labeling for reinforced learning is provided. With a majority of machine learning models, creating a large corpus of data to train on is essential. With regard to segmentation algorithms for labeling DICOMS, as described herein, the ability to create large amounts of data for robust algorithms is limited by the resources of skilled engineers or imaging specialists. By utilizing the initial results of segmentation algorithms, the methods described herein may speed up the time it takes to create a large dataset. For example:

Time to segment a single image (no automation)=10 seconds;
Assumption for robust algorithms—100,000 labeled images;
100,000 images segmented sequentially would take ~278 hours of time;

In a theoretical worked example, wherein the model was trained four times and algorithm training was linear:

0-25,000—~69 hours—train;
25,001-50,000 (25% completed by algorithm) 52 hours—retrain;
50,001-75,000 (50% completed by algorithm) 35 hours—retrain;
75,001-100,000 (75% completed by algorithm) 17 hours;
100,000 images segmented using hybrid of algorithm and skilled personnel—173 hours The above simplified examples indicates that the segmentation algorithm will be able to achieve the desired level of automation much faster with the aid of retraining. In addition, this may be taken one step further by retraining the algorithm after each dataset is added to the training set. This could be achieved by using cloud infrastructures and event driven serverless computing platforms, such as AWS Lambdas. Showing the user an updated set of labels after each retraining may dramatically reduce the time to create large amounts of data.

Moreover, most medical image segmentation applications require a very high level of accuracy, and thus, the medical images may be used in their original full resolution. However, in cases where there is an inherent need to look at the whole, or most of the, 3D scan in order to detect a pathology, e.g., an aneurysm, most 2D based approaches would not be sufficient. Further, due to limitations in current hardware or prohibitive costs a 3D approach may not be applied to the full resolution scans.

Thus, the methods described herein may down-sample the review volume to find key features by using a D-Unet based architecture to segment the vasculature in CT scans, e.g., neuro CT scans. This architecture looks at small stacks of 2D images, e.g., 4 slices below and 4 slices above, thereby providing some small 3D contextual information. In the case of aneurysm detection, the current approach may not be sufficient to distinguish between aneurysm and healthy vessels as it looks at only a few 2D images at a time, which may not be enough to achieve the context needed to be able to correctly identify aneurysms. This is mainly because the texture and general appearance of aneurysms is indistinguishable from other vasculature when looked at in isolation, e.g. in a few 2D images.

Being able to automatically identify and potentially locate and measure aneurysms, clots, and occlusions may revolutionize neurosurgery and save lives. For example, the methods described herein may use more advanced methods that can look at the whole scan from a 3D perspective in order to differentiate these abnormalities from the rest of the vasculature. Accordingly, the methods described herein may implement a two-step approach where the first step identifies the vasculature in the stack of images using a full resolution approach, and then a separate model would look at a low resolution version of the scan in three dimensions in the second step. After obtaining the region where the aneurysm is in the low resolution volume, the region may be co-registered with the high resolution version, such that the aneurysm may be segmented from the general vasculature segmentation. This approach has a lot of potential for other high resolution 3D volume applications where there is a need to distinguish between similarly textured elements which require a much larger context in order to be correctly identified.

The preparation of images for the purposes of generating a model (physical or virtual) using real life medical images requires a certain amount of pre-filtering and improvement in order to generate an accurate model. Thus, a number of transformations must be performed to the images in order to dramatically improve the ultimate model quality.

For example, interpolation of images may be very amenable as a large dataset of existing images may be used to train the algorithm. This type of problem is particularly suited to adversarial networks. Moreover, registration of images may be important as the number of cases that involve multiple scanning modalities is increasing, and this there may be a need to register CT→MRI images. For example, images from multiple scanning modalities may be registered by aligning two different datasets together, e.g., if a medical scan of a patient's head is provided and a tumor is wanted from an MRI scan and a bone is wanted from a CT scan, landmarks may be picked that are visible on both MRI and CT scan in order to register the pixels and voxels in the same position. Even MRI scans where the images have been taken in multiple perspectives/planes in a single session may require registration as the difference between the planes may produce significantly different views of the patient highlighting completely different aspects of the anatomy.

Focusing specifically on the integrations required to make the end-to-end possible rather than the individual processes themselves, the systems and methods described herein focuses on how to integrate data upstream and downstream of the platform.

This area may include all the integrations downstream such as the Electronic Medical/Health Records. Moreover, information from the EMR (potentially to associate with outcomes later c.f. Prognosis Section) may be collated, which would also include any upstream integrations such as with couriers or printing bureaus. Key to the value in this area is the idea of provenance of the data and showing the digital thread of the production of the model from data ingress right through to the manufactured object/virtual object and beyond.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for multi-schema analysis of patient specific anatomical features from medical images, the system comprising a server and configured to:
    receive medical images of a patient and metadata associated with the medical images indicative of a selected pathology;
    automatically process the medical images using a segmentation algorithm to label pixels of the medical images;
    use an anatomical feature identification algorithm to classify one or more patient specific anatomical features within the medical images based on the labeled pixels;
    extract an isolated patient specific anatomical feature comprising the selected pathology from the one or more patient specific anatomical features based on the metadata;
    generate an isolated 3D surface mesh model defining a surface of the isolated patient specific anatomical feature; and
    generate physiological information associated with the selected pathology for the isolated 3D surface mesh model.

2. The system of claim 1, wherein the segmentation algorithm is configured to generate scores indicative of a likelihood that the pixels were labeled correctly.

3. The system of claim 1, wherein the segmentation algorithm comprises at least one of a threshold-based, decision tree, chained decision forest, or neural network method.

4. The system of claim 1, wherein the anatomical feature identification algorithm is configured to probabilistically match associated groups of the labeled pixels against an anatomical knowledge dataset to classify the one or more patient specific anatomical features within the medical images.

5. The system of claim 1, wherein the physiological information associated with the selected pathology comprises at least one of diameter, volume, density, thickness, surface area, tortuosity, rate of growth, Hounsfield Unit standard deviation, or average.

6. The system of claim 1, wherein the system is configured to:
    analyze features of the isolated patient specific anatomical feature with an anatomical feature database to identify one or more landmarks of the isolated patient specific anatomical feature; and
    associate the one or more identified landmarks with the pixels of the medical images,
    wherein the generated isolated 3D surface mesh model defines the surface of the isolated patient specific anatomical feature comprising the one or more identified landmarks.

7. The system of claim 6, wherein the system is configured to:
    identify a guided trajectory for performing a surgical procedure from a surgical implement database based on the selected pathology and the one or more identified landmarks; and
    display the guided trajectory to a user.

8. The system of claim 1, wherein the system is configured to:
    analyze features of the isolated patient specific anatomical feature with an anatomical feature database to identify one or more landmarks of the isolated patient specific anatomical feature; and analyze features of the one or more identified landmarks with a reference fracture database to detect a fracture of the isolated patient specific anatomical feature, wherein the generated isolated 3D surface mesh model defines the surface of the isolated patient specific anatomical feature comprising the one or more identified landmarks and the detected fracture.

9. The system of claim 8, wherein the system is configured to match the isolated 3D surface mesh model of the isolated patient specific anatomical feature against the reference fracture database to classify the detected fracture.

10. The system of claim 1, wherein the system is configured to:

generate a 3D surface mesh model defining a surface of the one or more classified patient specific anatomical features; and extract the isolated 3D surface mesh model of the isolated patient specific anatomical feature comprising the selected pathology from the 3D surface mesh model based on the metadata to thereby extract the isolated patient specific anatomical feature comprising the selected pathology and generate the isolated 3D surface mesh model.

11. The system of claim 10, wherein the system is configured to:

delineate the one or more classified patient specific anatomical features into binary labels;

separate the binary labels into separate anatomical features; and map the separate anatomical features to original grey scale values of the medical images and remove background within the medical images, wherein the generated 3D surface mesh model defines a surface of the separate anatomical features, or comprises a volumetric render defined by mapping specific colors or transparency values to the one or more classified patient specific anatomical features.

12. The system of claim 1, wherein the system is configured to:

determine start and end points of the isolated patient specific anatomical feature;

take slices at predefined intervals along an axis from the start point to the end point;

calculate a cross-sectional area of each slice defined by a perimeter of the isolated patient specific anatomical feature;

extrapolate a 3D volume between adjacent slices based on the respective cross-sectional areas; and calculate an overall 3D volume of the isolated patient specific anatomical feature based on the extrapolated 3D volumes between adjacent slices to thereby generate physiological information associated with the selected pathology for the isolated 3D surface mesh model.

13. The system of claim 1, wherein the system is configured to:

determine start and end points of the isolated patient specific anatomical feature and a direction of travel from the start point to the end point;

raycast at predefined intervals along an axis in at least three directions perpendicular to the direction of travel and determine distances between intersections of each ray cast and the isolated 3D surface mesh model;

triangulate the distances between intersections of each ray cast and the isolated 3D surface mesh model to calculate a center point at each interval;

adjust the direction of travel at each interval based on a directional vector between adjacent calculated center points, such that raycasting at the predefined intervals occur in at least three directions perpendicular to the adjusted direction of travel at each interval; and calculate a centerline of the isolated patient specific anatomical feature based on the calculated center points from the start point to the end point to thereby generate physiological information associated with the selected pathology for the isolated 3D surface mesh model.

14. The system of claim 1, wherein the system is configured to:

calculate a centerline of the isolated patient specific anatomical feature;

determine start and end points of the isolated patient specific anatomical feature and a directional vector from the start point to the end point;

establish cutting planes at predefined intervals along the centerline based on the directional vector from the start point to the end point, each cutting plane perpendicular to a direction of travel of the centerline at each interval;

raycast in the cutting plane at each interval to determine a position of intersection on the isolated 3D surface mesh model from the centerline; and calculate a length across the isolated 3D surface mesh model based on the determined positions of intersection at each interval to thereby generate physiological information associated with the selected pathology for the isolated 3D surface mesh model.

15. The system of claim 1, wherein the system is configured to:

determine start and end points of the isolated patient specific anatomical feature;

take slices at predefined intervals along an axis from the start point to the end point;

calculate a cross-sectional area of each slice defined by a perimeter of the isolated patient specific anatomical feature; and generate a heat map of the isolated patient specific anatomical feature based on the cross-sectional area of each slice to thereby generate physiological information associated with the selected pathology for the isolated 3D surface mesh model.

16. The system of claim 1, wherein the system is configured to:

determine start and end points of the isolated patient specific anatomical feature;

calculate a centerline of the isolated patient specific anatomical feature;

determine a directional travel vector between adjacent points along the centerline;

calculate a magnitude of change of directional travel vectors between adjacent points along the centerline; and generate a heat map of the isolated patient specific anatomical feature based on the magnitude of change of directional travel vectors between adjacent points along the centerline to thereby generate physiological information associated with the selected pathology for the isolated 3D surface mesh model.

17. The system of claim 1, wherein the generated physiological information associated with the selected pathology for the isolated 3D surface mesh model comprises an associated timestamp, and wherein the system is configured to:

record the generated physiological information and the associated timestamp; and calculate changes between the recorded physiological information over time based on associated timestamps, indicative of progression of the selected pathology.

18. The system of claim 17, wherein the system is configured to:

calculate a magnitude of the changes between the recorded physiological information over time; and generate a heat map of the isolated patient specific anatomical feature based on the magnitude of the changes between the recorded physiological information over time.

19. The system of claim 1, wherein the system is configured to:

receive patient demographic data;

identify one or more medical devices from a medical device database based on the patient demographic data and the generated physiological information associated with the selected pathology for the isolated 3D surface mesh model; and display the identified one or more medical devices to a user.

20. The system of claim 1, wherein the system is configured to:

receive patient demographic data;

identify one or more treatment options from a surgical implement database based on the patient demographic data and the generated physiological information associated with the selected pathology for the isolated 3D surface mesh model; and display the identified one or more treatment options to a user.

21. The system of claim 1, wherein the system is further configured to 3D print a physical version of the isolated 3D surface mesh model.

22. The system of claim 1, wherein the selected pathology comprises a fracture, and wherein the isolated patient specific anatomical feature comprises at least a portion of a bone having the fracture.

23. The system of claim 1, wherein the selected pathology comprises osteoarthritis, and wherein the isolated patient specific anatomical feature comprises at least a portion of a bone having the osteoarthritis.

24. The system of claim 1, wherein the selected pathology comprises a blood clot, and wherein the isolated patient specific anatomical feature comprises at least a portion of a left atrial appendage or a blood vessel having the blood clot.

25. The system of claim 1, wherein the selected pathology comprises a defective heart valve, and wherein the isolated patient specific anatomical feature comprises at least a portion of a heart having the defective heart valve.

26. The system of claim 1, wherein the selected pathology comprises an aneurysm, and wherein the isolated patient specific anatomical feature comprises at least a portion of a blood vessel having the aneurysm.

27. The system of claim 1, wherein the selected pathology comprises a tumor mass, and wherein the isolated patient specific anatomical feature comprises at least a portion of a bone or tissue having the tumor mass.

28. The system of claim 1, wherein the selected pathology comprises a tear, and wherein the isolated patient specific anatomical feature comprises at least a portion of a tissue having the tear.

29. A method for multi-schema analysis of patient specific anatomical features from medical images, the method comprising:

receiving, by a server, medical images of a patient and metadata associated with the medical images indicative of a selected pathology;

automatically processing, by the server, the medical images using a segmentation algorithm to label pixels of the medical images;

using, by the server, an anatomical feature identification algorithm to classify one or more patient specific anatomical features within the medical images based on the labeled pixels;

extracting, by the server, an isolated patient specific anatomical feature comprising the selected pathology from the one or more patient specific anatomical features based on the metadata;

generating, by the server, an isolated 3D surface mesh model defining a surface of the isolated patient specific anatomical feature; and generating, by the server, physiological information associated with the selected pathology for the isolated 3D surface mesh model.

30. A non-transitory computer-readable memory medium configured to store instructions thereon that when loaded by at least one processor cause the at least one processor to:

receive medical images of a patient and metadata associated with the medical images indicative of a selected pathology;

automatically process the medical images using a segmentation algorithm to label pixels of the medical images;

use an anatomical feature identification algorithm to classify one or more patient specific anatomical features within the medical images based on the labeled pixels;

extract an isolated patient specific anatomical feature comprising the selected pathology from the one or more patient specific anatomical features based on the metadata;

generate an isolated 3D surface mesh model defining a surface of the isolated patient specific anatomical feature; and generate physiological information associated with the selected pathology for the isolated 3D surface mesh model.

\* \* \* \* \*